(12) United States Patent
Cheng et al.

(10) Patent No.: US 7,728,138 B2
(45) Date of Patent: Jun. 1, 2010

(54) BIS-TRIPHENYLSILYL COMPOUNDS AND THEIR APPLICATION ON ORGANIC ELECTRONIC DEVICE

(75) Inventors: Chien-Hong Cheng, Hsinchu (TW); Jin-Ju Lin, Hsinchu (TW); Hsiang-Jung Huang, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 70 days.

(21) Appl. No.: 11/943,282

(22) Filed: Nov. 20, 2007

(65) Prior Publication Data

US 2009/0131670 A1     May 21, 2009

(51) Int. Cl.
*C07F 7/08* (2006.01)
*H01L 51/50* (2006.01)

(52) U.S. Cl. ............... 546/14; 428/690; 428/917; 556/431; 556/432

(58) Field of Classification Search ............... 556/432, 556/431; 428/690, 917; 546/14
See application file for complete search history.

(56) References Cited

U.S. PATENT DOCUMENTS

| | | | | |
|---|---|---|---|---|
| 6,808,826 | B2 * | 10/2004 | Kim et al. | 428/690 |
| 7,244,518 | B2 * | 7/2007 | Yu et al. | 428/690 |
| 7,479,330 | B2 * | 1/2009 | Yu et al. | 428/690 |
| 2006/0177691 | A1 * | 8/2006 | Tai et al. | 428/690 |

OTHER PUBLICATIONS

Gilman, H. et al.: The synthesis of some organosilicon compounds, particularly those containing halophenyl groups. J. Org. Chem. vol. 27, pp. 1023-1026, 1962.*
Ultrahigh Energy Gap Hosts in Deep Blue Organic Electrophosphorescent Devices., Ren, X.; Li, J.; Holmes, R. J.; Djurovich, P. I.; Forrest, S. R.; Thompson, M. E. Chem. Mater. 2004, 16, 4743.

New Dopant and Host Materials for Blue-Light-Emitting Phosphorescent Organic Electroluminescent Devices., Yeh, S. J.; Wu, M. F.; Chen, C. T.; Song, Y.-H.; Chi, Y.; Ho, M. H.; Hsu, S.-F.; Chen, C. H. Adv. Mater. 2005, 17, 285.
Highly Efficient Organic Blue Electrophosphorescent Devices Based on 3,6-Bis(triphenylsilyl)carbazole as the Host Material., Tsai, M.-H.; Lin, H.-W.; Su, H.-C.; Ke, T.-H.; Wu, C.-C.; Fang, F.-C.; Liao, Y.-L.; Wong, K.-T.; Wu, C.-I. Adv. Mater. 2006, 18, 1216.
Synthesis and Structure of 2,6,14- and 2,7,14- Trisunstituted Triptycene Derivatives., Chun Zhang; Chuan-Feng Chen, J. Org. Chem. 2006, 71, 6626-6629.

* cited by examiner

*Primary Examiner*—Charanjit S Aulakh
(74) *Attorney, Agent, or Firm*—WPAT, PC; Justin King

(57) ABSTRACT

The present invention discloses a bis-triphenylsilyl compound and its applications as a host material, electron transport material, or hole transport material in an organic electronic device. The general structure of the bis-triphenylsilyl compound is as follows:

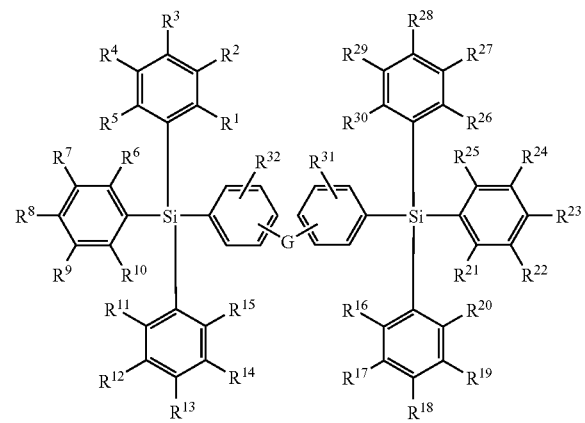

where G represents any atomic moiety or single bond of the functional group selected from the group consisting of the following: aryl group, cyclene group, and heterocyclic ring group; and $R^1 \sim R^{32}$ represent substituents on aryl groups.

19 Claims, 12 Drawing Sheets

US 7,728,138 B2

BIS-TRIPHENYLSILYL COMPOUNDS AND THEIR APPLICATION ON ORGANIC ELECTRONIC DEVICE

BACKGROUND OF THE INVENTION

1. Field of the Invention

The present invention is generally related to an aromatic conjugated compound, and more particularly to a bis-triphenylsilyl compound and its application on organic electronic devices.

2. Description of the Prior Art

At present, phosphorescent metal complexes have been used as phosphorescent dopants in an organic light emitting diode. Among these metal complexes used in the light-emitting layer of the organic light emitting diode, cyclometalated iridium complexes have been extensively researched since their electron configurations have strong spin-orbit coupling. Since spin-orbit coupling results in mixing between the singlet and triplet excited states, the lifetime of the triplet state is greatly reduced and thereby the phosphorescence efficiency is promoted. In addition, it is found that the doping method can also enhance the efficiency of the device. Therefore, the method of doping phosphorescent substance in a host material is utilized and thus the research[1-3] in blue phosphorescent host materials becomes important. In view of the above matter, developing a novel organic compound having high heat stability and high triplet-state energy to prolong the usage lifetime of the device and to increase luminance efficiency is still an important task for the industry.

SUMMARY OF THE INVENTION

In light of the above background, in order to fulfill the requirements of the industry, the present invention provides a novel bis-triphenylsilyl compound and its application as a host material, an electron transport material, or a hole transport material in an organic electronic device.

One object of the present invention is to provide a bis-triphenylsilyl compound having high thermal stability to promote the lifetime of an organic electronic device.

Another object of the present invention is to provide a bis-triphenylsilyl compound having high triplet-state energy difference, which can not be reached by the general blue phosphorescence host materials, and can be used together with various common phosphorescent materials, such as blue, green, and red phosphorescent materials, like iridium (Ir), platinum (Pt), and osmium (Os) metal complexes. Therefore, this present invention does have the economic advantages for industrial applications.

Accordingly, the present invention discloses a bis-triphenylsilyl compound. The bis-triphenylsilyl compound has the following general structure:

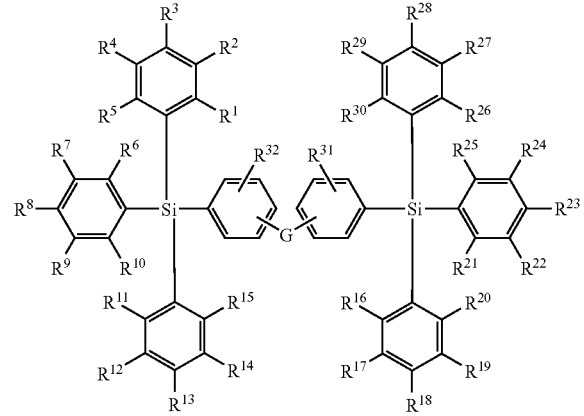

where G represents any atomic moiety or single bond of the functional group selected from the group consisting of the following: aryl group, cyclene group, and heterocyclic ring group; and $R^1 \sim R^{32}$ represent substituents on aryl groups.

The invention also discloses the application of the bis-triphenylsilyl compound, especially the application as a light-emitting host material, an electron transport material, or a hole transport material in an organic electroluminescence device or phosphorescence device; or the application as an electron transport material or a hole transport material in other organic electronic devices.

DESCRIPTION OF THE PREFERRED EMBODIMENTS

Figure 1:
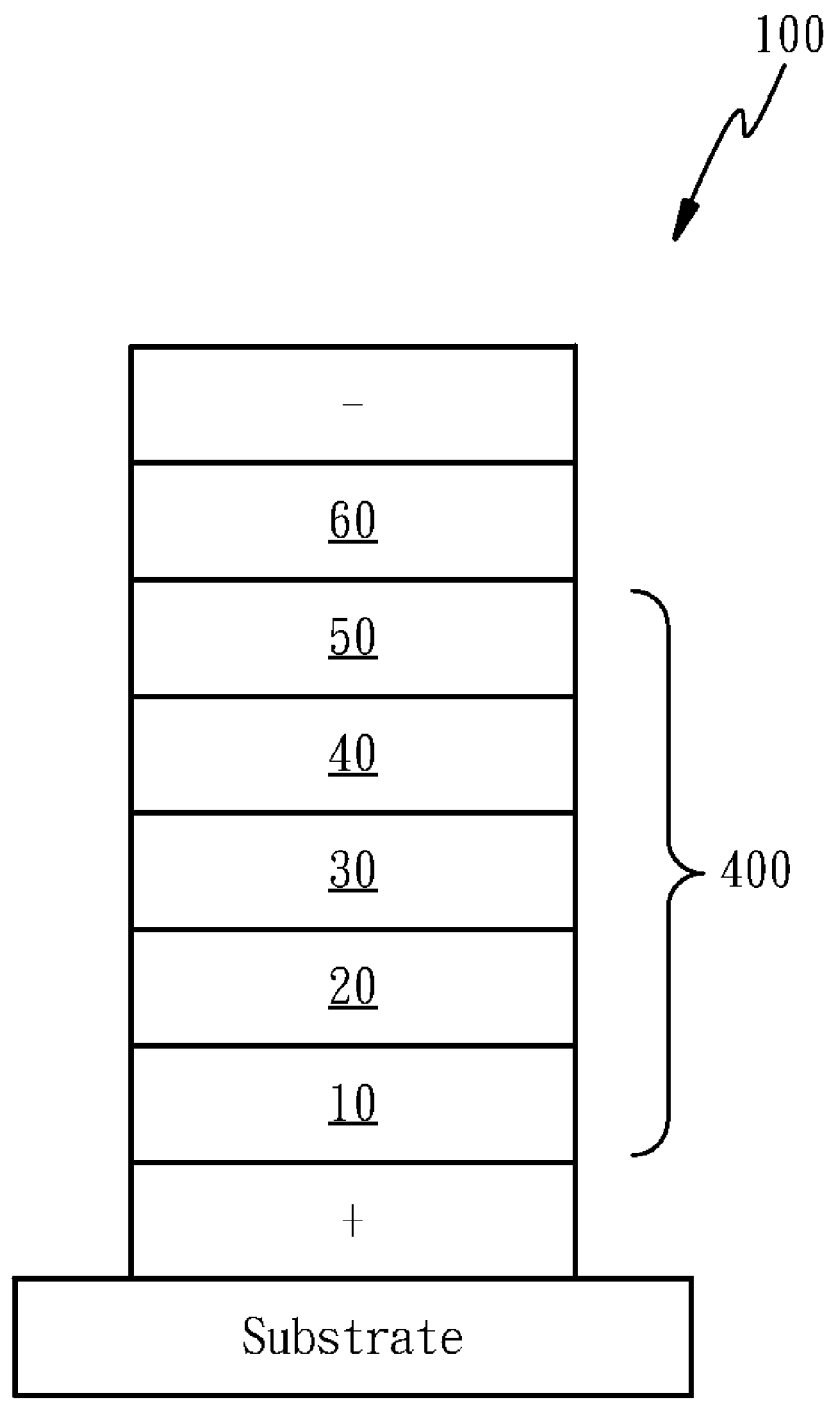
FIG. 1 shows a structural schematic diagram illustrating a multi-layer organic light emitting device according to the invention.
Figure 2:
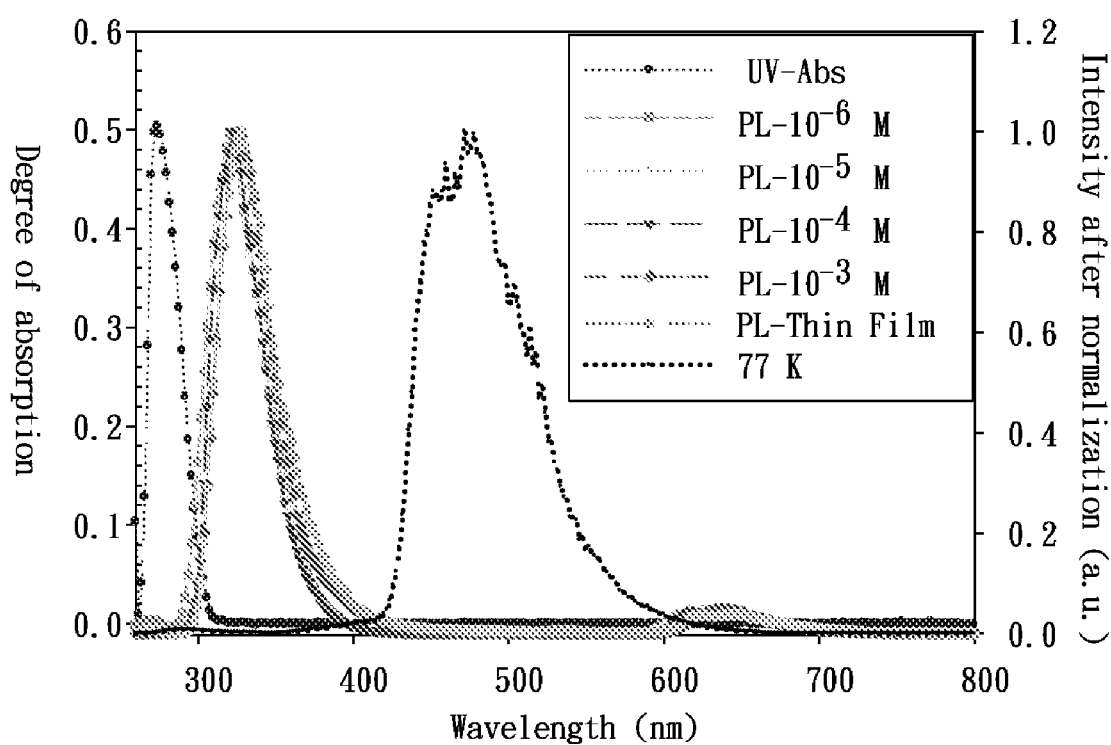
FIGS. 2~8 show absorption and emission spectra of examples 2~8, respectively.
Figure 3:
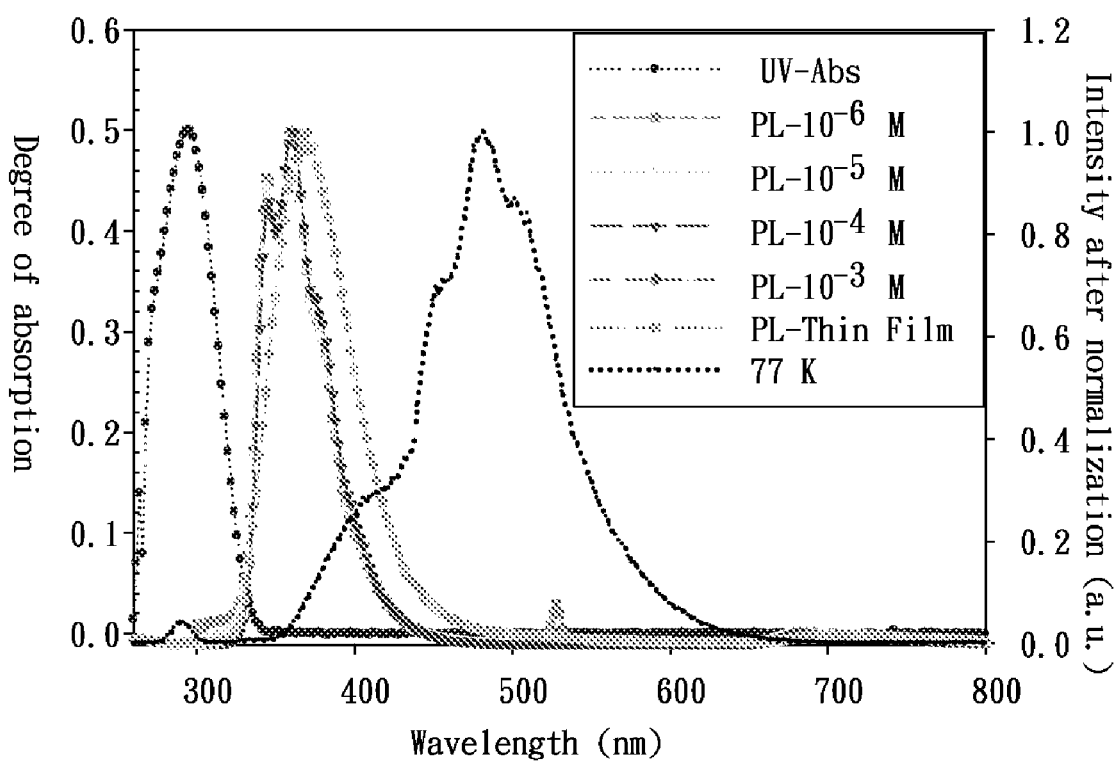
Figure 4:
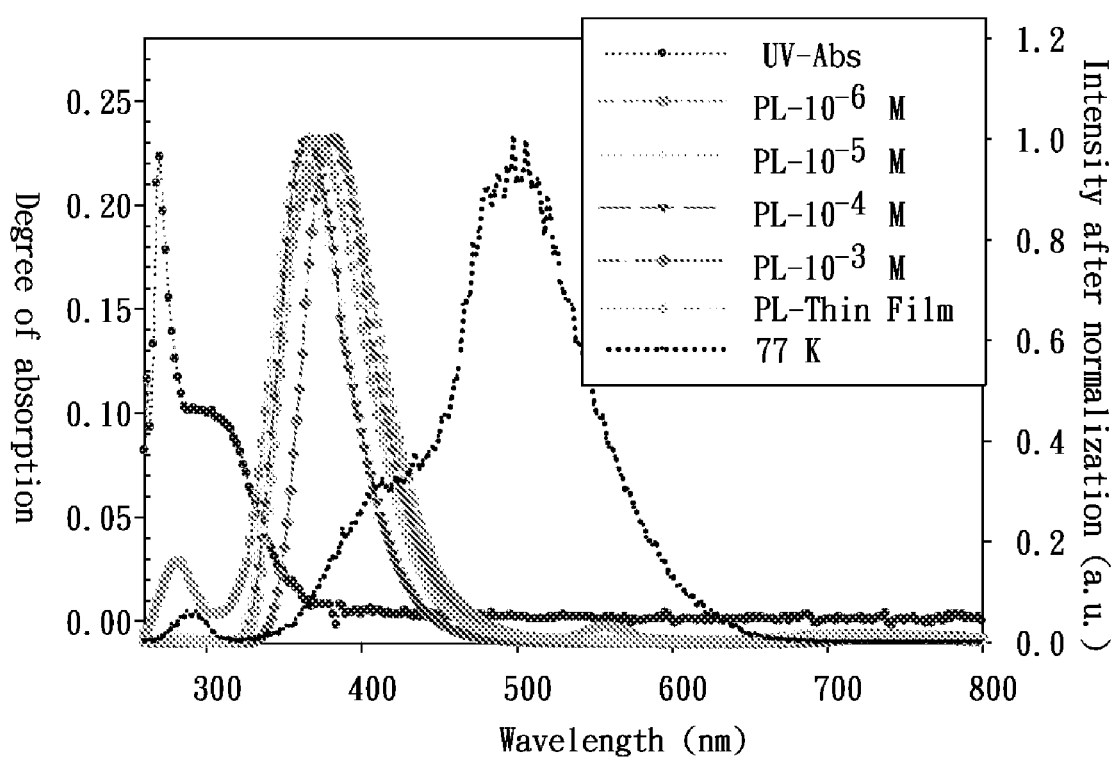
Figure 5:
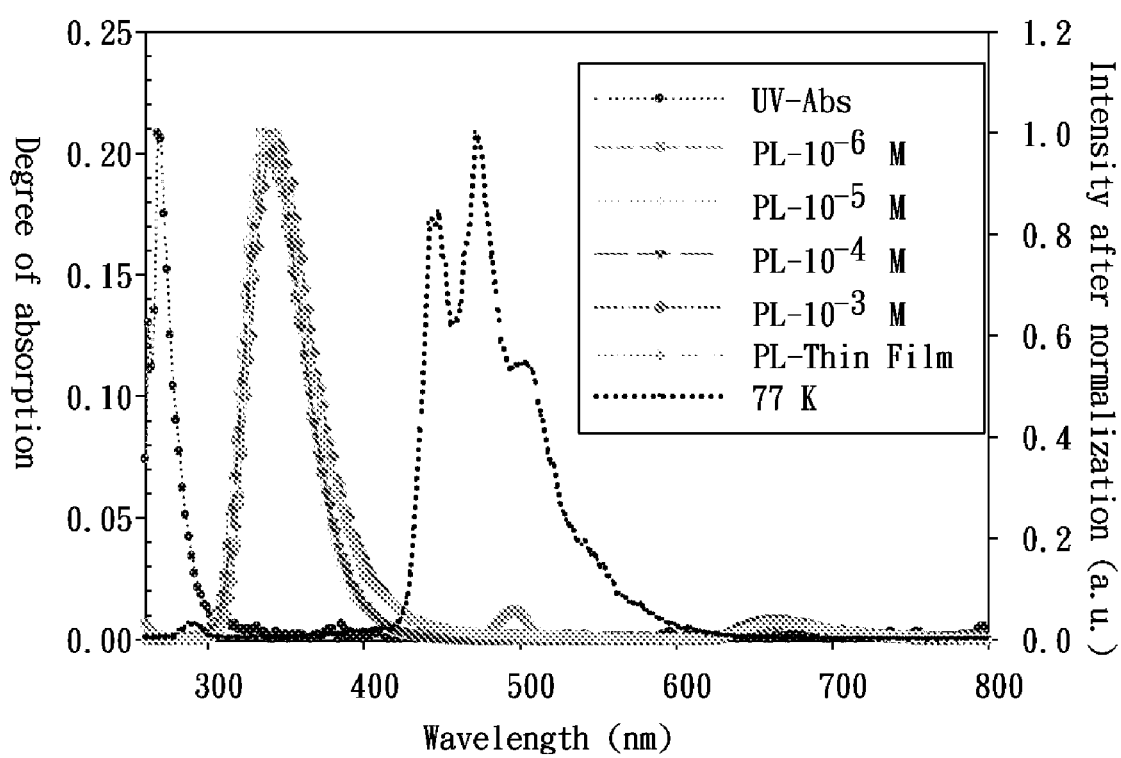
Figure 6:
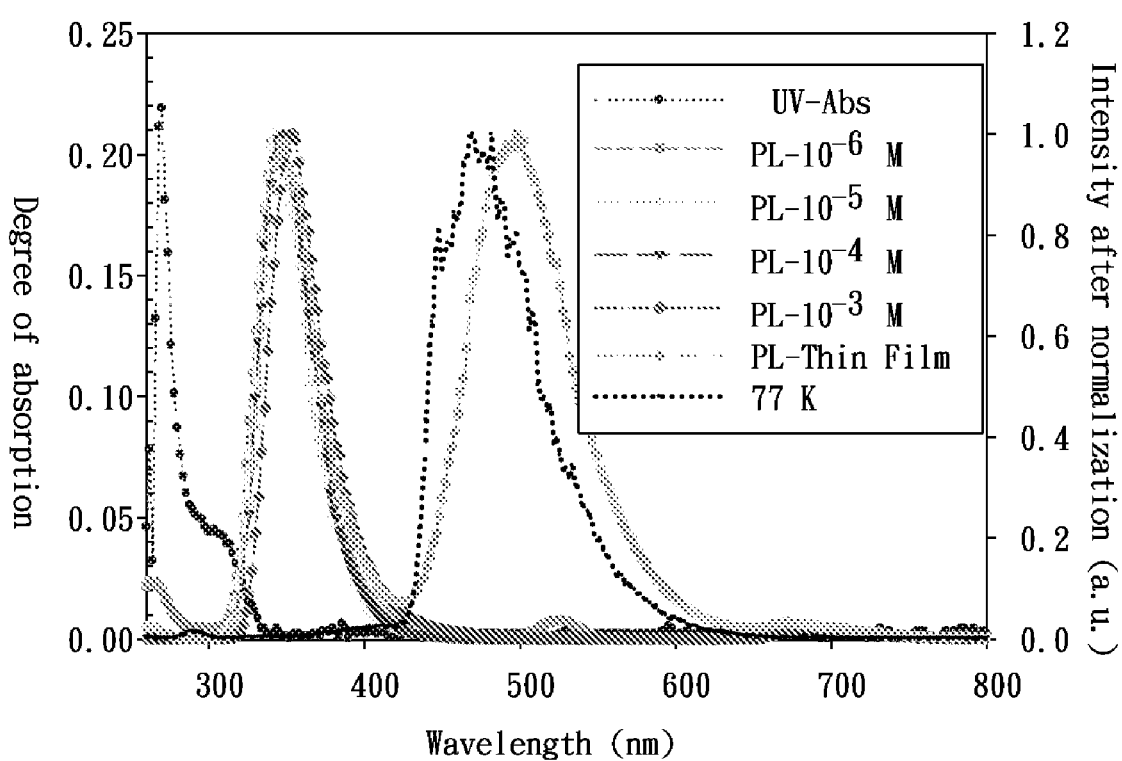
Figure 7:
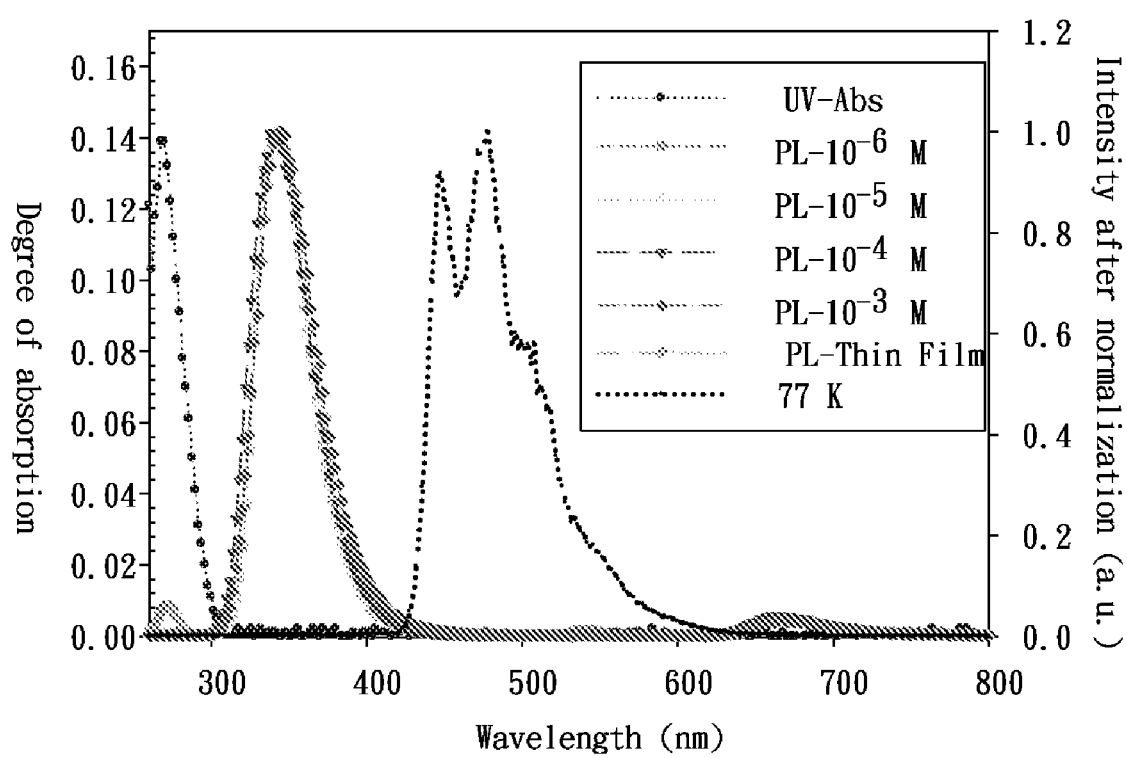
Figure 8:
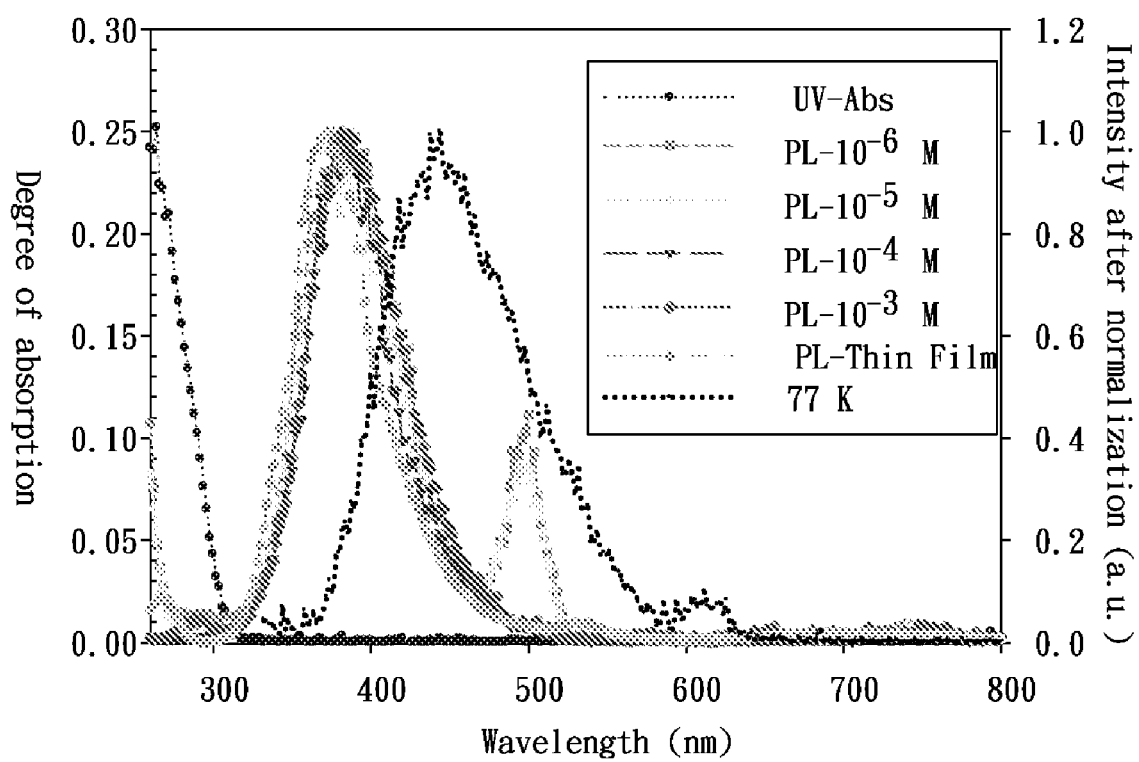
Figure 9:
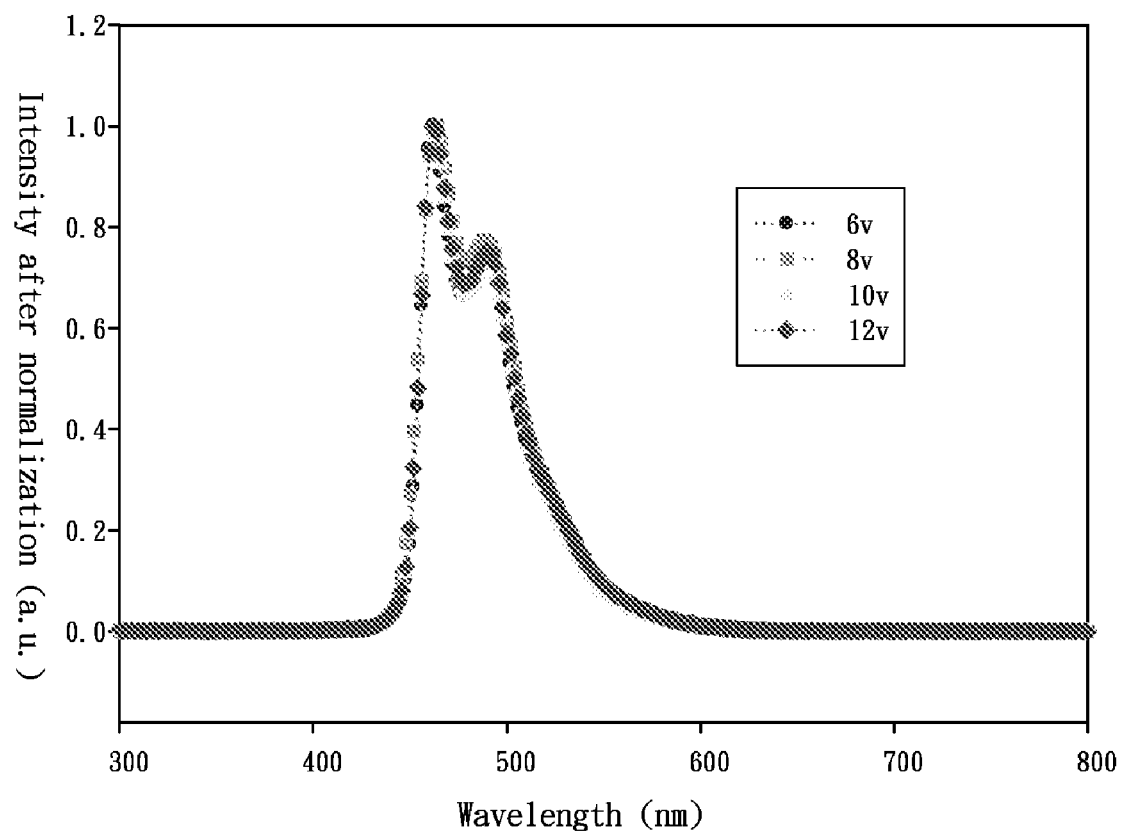
FIG. 9 shows electroluminescence and CIE coordinate diagram of the device E.
Figure 10:
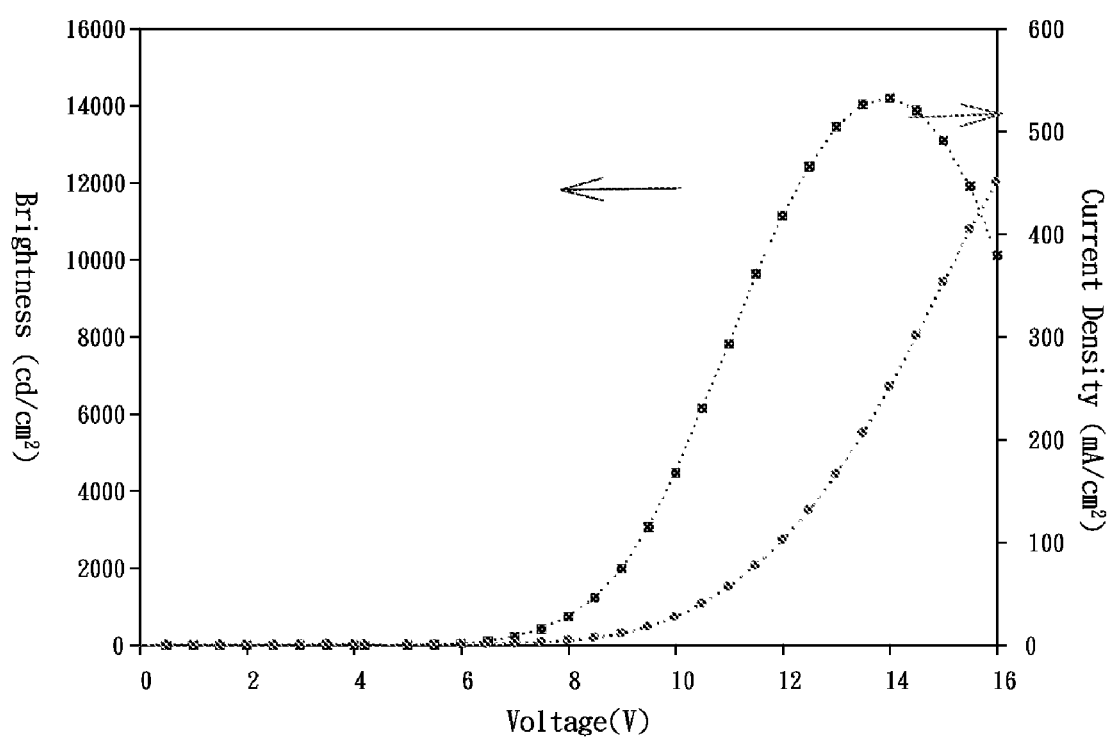
FIG. 10 is a diagram showing the dependence of candela and current density versus voltage.
Figure 11:
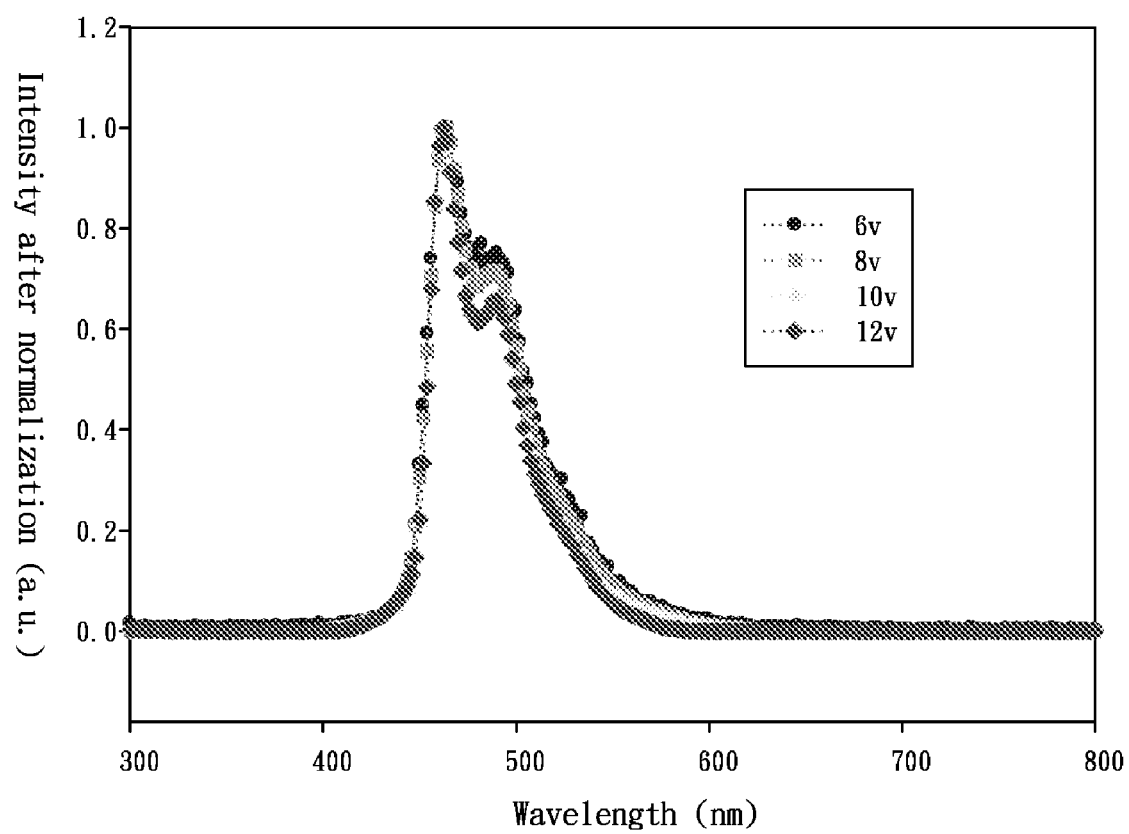
FIG. 11 shows electroluminescence and CIE coordinate diagram of the device F.
Figure 12:
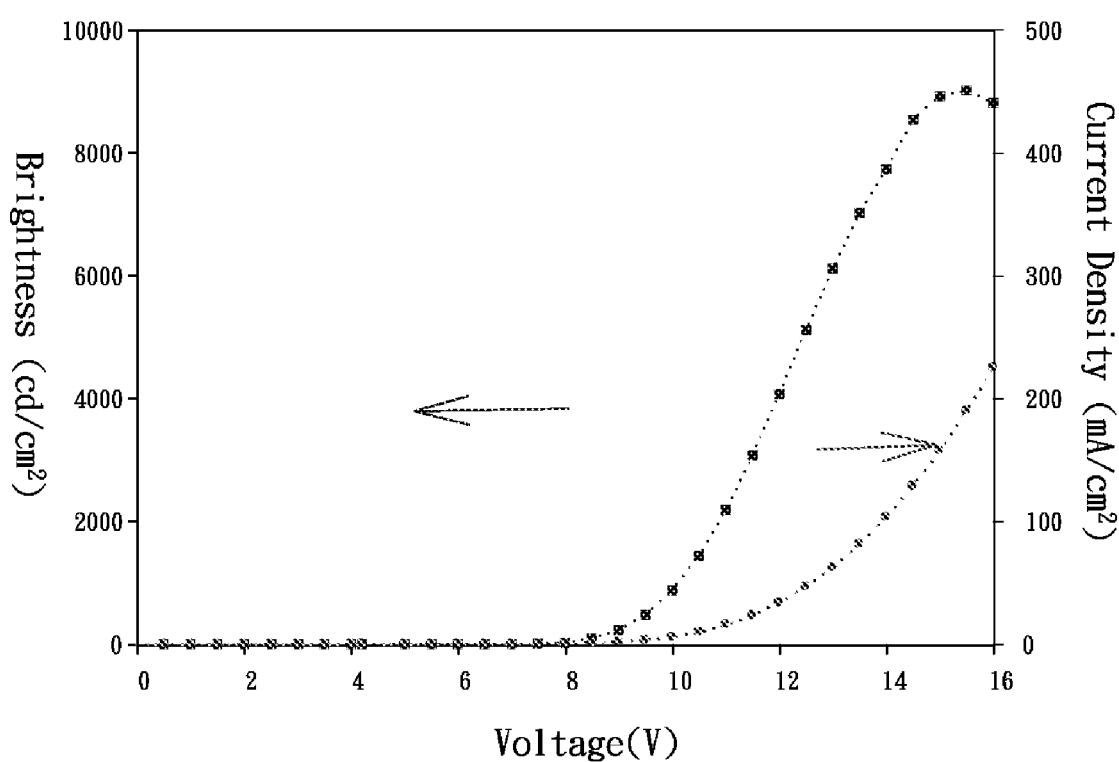
FIG. 12 is a diagram showing the dependence of candela and current density versus voltage for the device F.

What is probed into the invention is a bis-triphenylsilyl compound. Detail descriptions of the processes and composition structures will be provided in the following in order to make the invention thoroughly understood. Obviously, the application of the invention is not confined to specific details familiar to those who are skilled in the art. On the other hand, the common processes and composition structures that are known to everyone are not described in details to avoid unnecessary limits of the invention. Some preferred embodiments of the present invention will now be described in greater detail in the following. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

In a first embodiment of the present invention, the structure of a bis-triphenylsilyl compound is disclosed. The bis-triphenylsilyl compound has the following general structure:

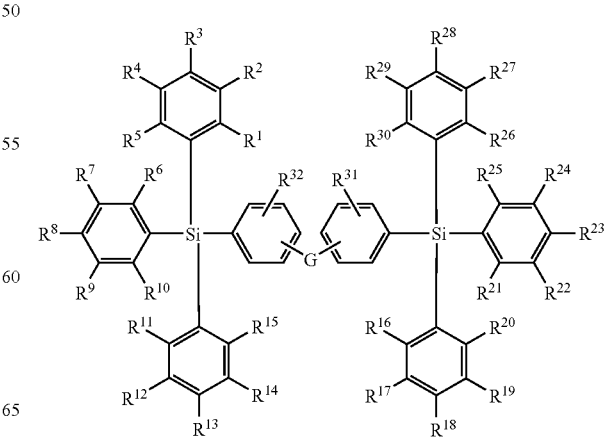

The above G represents any atomic moiety or single bond of aryl group, cyclene group, or heterocyclic ring group. As G represents a single bond, in the above mentioned structure, aryl groups on the two sides of G is bonded with one single bond. The aryl group, cyclene group, or heterocyclic ring group each can comprise at least one substituent. The substituent is selected from the group consisting of the following: H atom, halogen atom (such as F, Cl, Br, I); aryl group; halogen substituted aryl group; C1-C20 haloalkyl substituted aryl group; C1-C20 haloalkyl substituted aralkyl group; aryl substituted C1-C20 alkyl group; C1-C20 alkyl group, C1-C20 cycloalkyl group (such as methyl, ethyl, butyl, cyclohexyl); C1-C20 alkoxy group; amino group; aryl substituted amino group; C1-C20 alkyl substituted amino group; nitrile group; nitro group; carbonyl group; cyano group (—CN); substituted aromatic amino group; aryl phosphoryl (P=O) group; Si-containing aryl group; and heterocyclic ring group.

The above $R^1 \sim R^{32}$ can be identical or different and $R^1 \sim R^{32}$ are independently selected from the group consisting of the following: H atom, halogen atom (such as F, Cl, Br, I); aryl group; halogen substituted aryl group; C1-C20 haloalkyl substituted aryl group; aralkyl group; C1-C20 haloalkyl substituted aralkyl group; aryl substituted C1-C20 alkyl group; C1-C20 alkyl group, C1-C20 cycloalkyl group (such as methyl, ethyl, butyl, cyclohexyl); C1-C20 alkoxy group; amino group; aryl substituted amino group; C1-C20 alkyl substituted amino group; nitrile group; nitro group; carbonyl group; cyano group (—CN); substituted aromatic amino group; aryl phosphoryl (P=O) group; Si-containing aryl group; and heterocyclic ring group.

The aryl group comprises phenyl, naphthyl, diphenyl, anthryl, pyrenyl, phenanthryl, fluorene, or other multi-phenyl group.

The heterocyclic ring group can be pyrane, pyrroline, furan, benzofuran, thiophene, benzothiophene, pyridine, quinoline, isoquinoline, pyrazine, pyrimidine, pyrrole, pyrazole, imidazole, indole, thiazole, isothiazole, oxazole, isoxazole, benzothiazole, benzoxazole, 1,2,4-triazole, 1,2,3-triazole, 1,2,3,4-tetraazole, phenanthroline, or other heterocyclic aryl group.

The preferred examples of the structure and fabricating method for the bis-triphenylsilyl compound according to the invention are described in the following. However, the scope of the invention should be based on the claims, but is not restricted by the following examples.

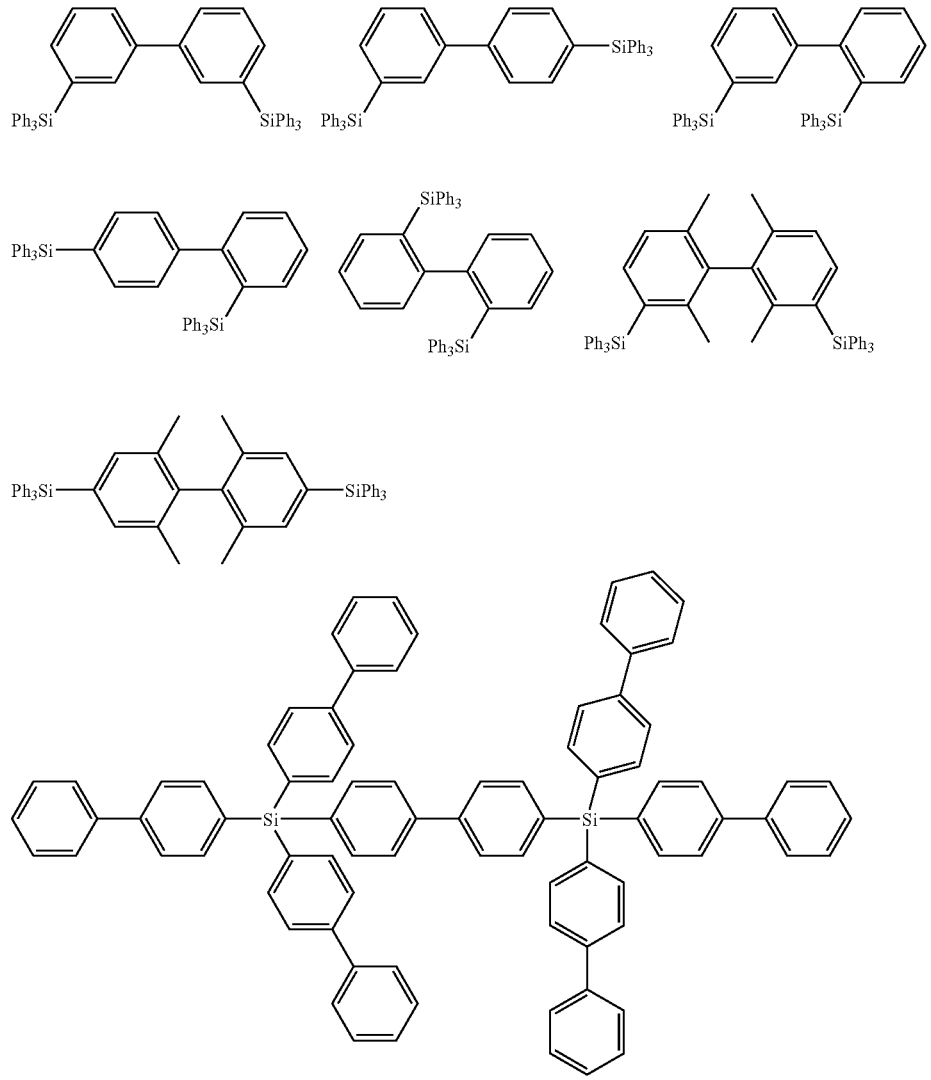

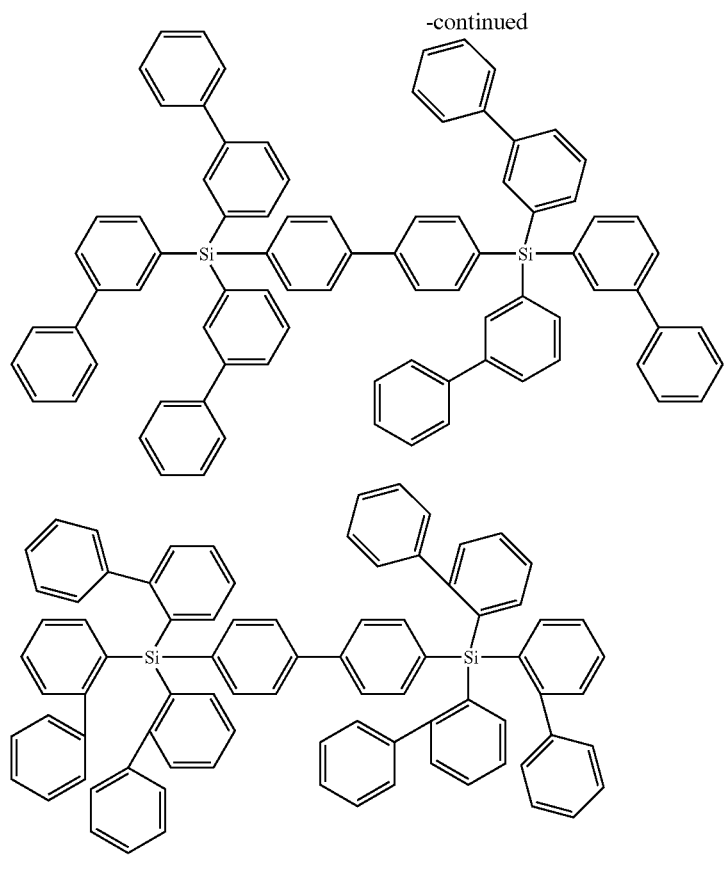

EXAMPLE 1

Method for forming a bis-triphenylsilyl compound:

Scheme 1

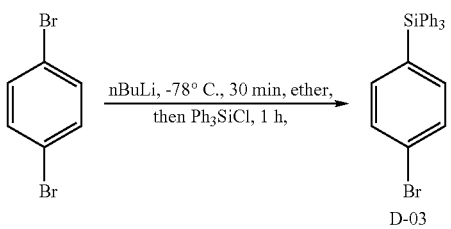

At first, as shown in Scheme 1, p-dibromobenzene (10 mmole) is placed in a reaction flask and dissolved in 40 ml of ether. After the reaction flask is cooled to −78° C., n-butyl lithium (10 mmole) is gradually added into the reaction flask to form a lithium reagent. Separately, triphenylsilyl chloride (10 mmole) is dissolved in 40 ml of ether. After cooled to −78° C., this ether solution is added into the reaction flask that contains the lithium reagent. At −78° C., the reaction is carried out for 3 hrs. Then, the temperature of the reaction flask is returned to room temperature. The reaction is carried out for 1 hr at room temperature. After the reaction is finished, 4N hydrochloric acid solution is added. The suction filtration is used to separate solids. White solids D-03 are obtained [$^1$H NMR (400 MHz, CDCl$_3$): δ 7.51-7.53 (m, 6H), 7.49-7.50 (m, 2H), 7.35-7.44 (m, 11H)].

Scheme 2

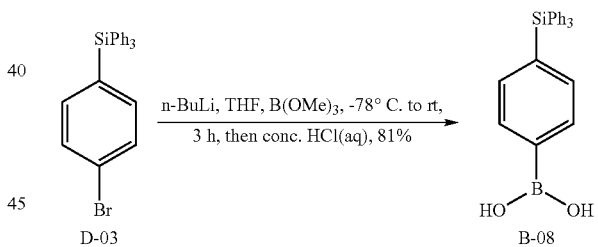

Then, as shown in Scheme 2, the compound D-03(10 mmole) is dissolved in 40 mL of THF (tetrahydrofuran). In the nitrogen environment and at −78° C., n-butyl lithium (10 mmole) is gradually added and the reaction is carried out for 30 minutes to form an organic lithium reagent. At the same temperature, trimethyl borate (10 mmole) is added. The temperature of the reaction flask is gradually returned to room temperature. After the reaction is finished, 10% hydrochloric acid solution is added and extraction by ethyl acetate is carried out. The organic layer is treated with anhydrous magnesium sulfate to remove water content and then the solvent in the organic layer is removed by a rotary evaporator. Thus, white solids, i.e. the compound B-08, are obtained [$^1$H NMR (400 MHz, CDCl$_3$): δ 8.18 (d, 2 H, J=7.2 Hz), 7.71 (d, 2 H, J=7.2 Hz), 7.54-7.62 (m, 6 H), 7.36-7.43 (m, 9 H)].

Finally, in the nitrogen environment, the compound B-08 (10 mmol), dibromo compound or D-03 (5 mmol), and Pd(PPh$_3$)$_4$ (0.2 mmole) are dissolved in 50 mL of deoxygenated toluene, 4 mL of ethanol, and 10 mL of 2M potassium carbonate solution. The mixture is heated to 80° C. and the reaction is carried out for 24 hrs. After the reaction is finished, 50 mL of ethyl acetate is added. The organic layer is filtered by tripoli and is treated with anhydrous magnesium sulfate to remove water content. Then, the solvent in the organic layer is removed to obtain solids. The solids are sequentially washed by distilled water, methanol, and ether. Thus, the bis-triphenylsilyl compound is obtained.

EXAMPLE 2

(4,4'-Bis-triphenylsilanyl-biphenyl; hereinafter abbreviated as BSB)

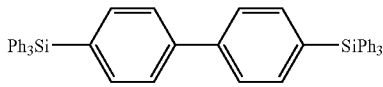

$^1$H NMR (400 M Hz, CDCl$_3$): δ 7.36-7.43 (m, 18 H), 7.59-7.63 (m, 20 H). $^{13}$C NMR (100 M Hz, CDCl$_3$): δ 126.5 (CH), 127.9 (CH), 129.6 (CH), 133.3 (C), 134.2 (C), 136.4 (CH), 136.9 (CH), 141.9 (C). MS (EI, m/z): 670 (M$^+$). Anal. Calcd. for C$_{48}$H$_{38}$Si$_2$: C, 85.92; H, 5.71%. Found: C, 85.52; H, 5.92%.

EXAMPLE 3

(4,4"-Bis-triphenylsilanyl-[1,1';4',1"]terphenyl; hereinafter abbreviated as pBST)

$^1$H NMR (600 M Hz, CDCl$_3$): δ 7.36-7.43 (m, 18 H), 7.57-7.62 (m, 12 H), 7.64 (s, 8 H), 7.69 (s, 4 H). $^{13}$C NMR (150 M Hz, CDCl$_3$): δ 126.4 (CH), 127.5 (CH), 127.9 (CH), 129.6 (CH), 133.2 (C), 134.2 (C), 136.4 (CH), 136.9 (CH), 140.0 (C), 141.6 (C). HRMS (EI, m/z): calcd for C$_{54}$H$_{42}$Si$_2$ 746.2825, found 746.2819 (M$^+$). Anal. Calcd. for C$_{54}$H$_{42}$Si$_2$C, 86.81; H, 5.67%. Found: C, 86.71; H, 5.34%.

EXAMPLE 4

[2,5-Bis-(4-triphenylsilanyl-phenyl)-pyridine; hereinafter abbreviated as pBSP]

$^1$H NMR (400 M Hz, CDCl$_3$): δ 7.38-7.45 (m, 18 H), 7.59-7.70 (m, 18 H), 7.81 (d, J=8 Hz, 1 H), 7.97 (d, 1 H, J=8 Hz), 8.03 (d, 2 H, J=8 Hz), 8.96 (s, 1 H). $^{13}$C NMR (100 M Hz, CDCl$_3$): δ 120.5 (CH), 126.2 (CH), 126.3 (CH), 127.9 (CH), 128.0 (CH), 129.6 (CH), 129.7 (CH), 133.9 (CH), 134.0 (CH), 134.3 (C), 134.8 (C), 135.1 (C), 135.3 (C), 136.4 (CH), 136.9 (CH), 137.1 (CH), 138.6 (C), 140.0 (C), 148.2 (C), 156.2 (C). HRMS (FAB, m/z): calcd for C$_{53}$H$_{41}$NSi$_2$ 747.2778, found 748.2858 (M+H$^+$). Anal. Calcd. for C$_{53}$H$_{41}$NSi$_2$C, 85.09; H, 5.52%; N, 1.87. Found: C, 85.19; H, 5.52; N, 1.63%.

EXAMPLE 5

(4,4"-Bis-triphenylsilanyl-[1,1';3',1"]terphenyl; hereinafter abbreviated as mBST)

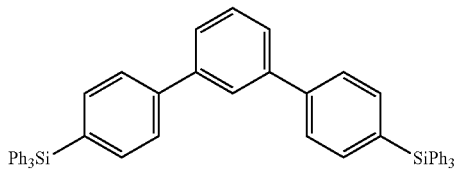

$^1$H NMR (400 M Hz, CDCl$_3$): δ 7.38-7.47 (m, 18 H), 7.52 (t, 1 H, J=7.2 Hz), 7.60-7.62 (m, 14 H), 7.66 (s, 8 H), 7.86 (s, 1 H). $^{13}$C NMR (100 M Hz, CDCl$_3$): δ 126.2 (CH), 126.3 (CH), 126.6 (CH), 127.9 (CH), 129.3 (CH), 129.6 (CH), 133.2 (C), 134.1 (C), 136.4 (CH), 136.9 (CH), 141.5 (C), 142.1 (C). HRMS (EI, m/z): calcd for C$_{54}$H$_{42}$Si$_2$ 746.2825, found 746.2816 (M$^+$). Anal. Calcd. for calcd for C$_{54}$H$_{42}$Si$_2$C, 86.81; H, 5.67%. Found: C, 86.44; H, 5.15%.

EXAMPLE 6

(2,6-Bis-(4-triphenylsilanyl-phenyl)-pyridine; hereinafter abbreviated as mBSP)

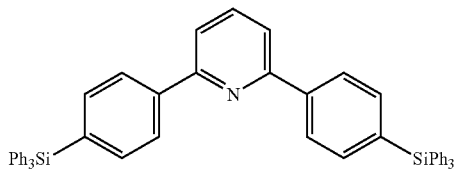

$^1$H NMR (400 MHz, CDCl$_3$): δ 7.35-7.45 (m, 18 H), 7.58-7.60 (m, 12 H), 7.67-7.71 (m, 6 H), 7.81 (dd, 1 H, J=8.4, 6.8 Hz), 8.12 (d, 4 H, 8.4 Hz). $^{13}$C NMR (100 M Hz, CDCl$_3$): δ 119.0 (CH), 126.3 (CH), 127.9 (CH), 129.6 (CH), 134.1 (C), 135.2 (C), 136.4 (CH), 136.8 (CH), 137.5 (CH), 140.5 (C), 156.8 (C). HRMS (FAB, m/z): calcd for C$_{53}$H$_{41}$NSi$_2$ 747.2778, found 748.2849 (M+H$^+$). Anal. Calcd. for calcd for C$_{53}$H$_{41}$NSi$_2$C, 85.09; H, 5.52%; N, 1.87. Found: C, 84.73; H, 5.33; N, 1.78%.

EXAMPLE 7

(5'-Methyl-4,4"-bis-triphenylsilanyl-[1,1';3',1"]terphenyl; hereinafter abbreviated as mBST-Me)

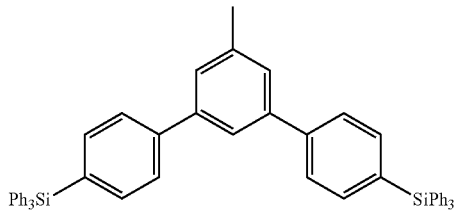

$^1$H NMR (400 MHz, CDCl$_3$): δ 2.51 (s, 3 H), 7.40-7.47 (m, 20 H), 7.64-7.69 (m, 21 H). $^{13}$C NMR (100 M Hz, CDCl$_3$): δ 21.6 (CH$_3$), 123.4 (CH), 126.7 (CH), 127.2 (CH), 127.9 (CH), 129.6 (CH), 133.0 (C), 134.2 (C), 136.4 (CH), 136.9 (CH), 138.8 (C), 141.5 (C), 142.3 (C). HRMS (FAB, m/z): calcd for C$_{55}$H$_{44}$Si$_2$ 760.2982, found 760.2984 (M$^+$). Anal. Calcd. for calcd for C$_{55}$H$_{44}$Si$_2$C, 86.79; H, 5.83%. Found: C, 86.92; H, 5.72%.

EXAMPLE 8

(4,4"-Bis-triphenylsilanyl-[1,1';2',1"]terphenyl; hereinafter abbreviated as oBST)

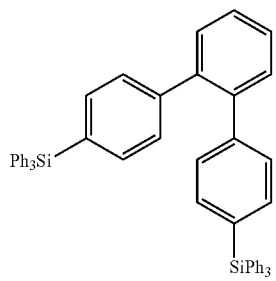

$^1$H NMR (400 MHz, CDCl$_3$): δ 7.18 (d, 4 H, J=8 Hz), 7.28-7.32 (m, 12 H), 7.37-7.49 (m, 14 H), 7.53-7.55 (m, 12 H). $^{13}$C NMR (100 MHz, CDCl$_3$): δ 127.7 (CH), 127.9 (CH), 129.4 (CH), 129.5 (CH), 130.4 (CH), 132.1 (C), 134.2 (C), 135.8 (CH), 136.3 (CH), 140.5 (C), 142.6 (C). HRMS (EI, m/z): calcd for C$_{54}$H$_{42}$Si$_2$ 746.2825, found 746.2796(M$^+$). Anal. Calcd. for calcd for C$_{54}$H$_{42}$Si$_2$ C, 86.81; H, 5.67%. Found: C, 86.74; H, 5.62 %.

EXAMPLE 9

(2',4',5',6'-Tetrafluoro-4,4"-bis-triphenylsilanyl-[1,1';3',1"]terphenyl; hereinafter abbreviated as mBST-F)

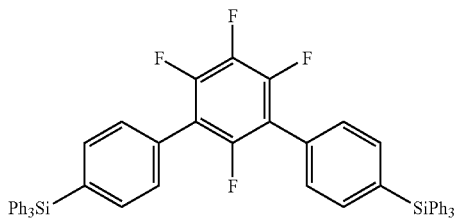

$^1$H NMR (400 M Hz, CDCl$_3$): δ 7.36-7.46 (m, 22 H), 7.57-7.60 (m, 12 H), 7.66-7.68 (m, 4 H). Anal. Calcd. for calcd for C$_{54}$H$_{38}$F$_4$Si$_2$ C, 79.19; H, 4.68. Found: C, 79.03; H, 4.47%.

EXAMPLE 10

(2',5'-Dimethyl-4,4"-bis-triphenylsilanyl-[1,1';4',1"]terphenyl; hereinafter abbreviated as pBST-DM)

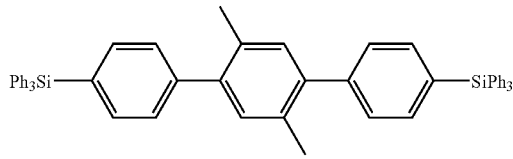

$^1$H NMR (400 MHz, CDCl$_3$): δ 2.28 (s, 6 H), 7.16 (s, 2 H), 7.36-7.43 (m, 22 H), 7.59-7.61 (m, 16 H). Anal. Calcd. for calcd for C$_{56}$H$_{46}$Si$_2$ C, 86.77; H, 5.98. Found: C, 86.80; H, 5.94%.

EXAMPLE 11

(2',3',5',6'-Tetramethyl-4,4"-bis-triphenylsilanyl-[1,1';4',1"]terphenyl; hereinafter abbreviated as pBST-TM)

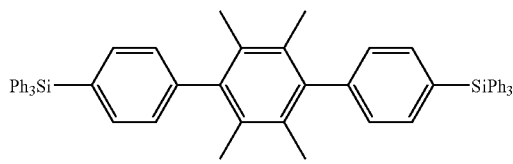

$^1$H NMR (400 MHz, CDCl$_3$): δ 1.96(s, 12 H), 7.20 (d, 4 H, J=8 Hz), 7.37-7.44 (m, 22H), 7.60-7.63 (m, 16 H). $^{13}$C NMR (150 M Hz, CDCl$_3$): δ 18.2(CH$_3$), 127.9 (CH), 129.0 (CH), 129.6 (CH), 131.7 (C), 131.8 (C), 134.3 (C), 136.3 (CH), 136.4 (CH), 141.0 (C), 144.0 (C). Anal. Calcd. for calcd for C$_{58}$H$_{50}$Si$_2$ C, 86.73; H, 6.27. Found: C, 86.36; H, 6.27%.

According to this embodiment, the bis-triphenylsilyl compound has excellent heat stability and high triplet-state energy difference. Therefore, as the bis-triphenylsilyl compound is applied in an organic electronic device, the excellent heat stability makes the lifetime of the organic electronic device increased. Furthermore, as the bis-triphenylsilyl compound is applied in an organic electroluminescence device, the bis-triphenylsilyl compound has high triplet-state energy difference, which can not be provided by the existing known blue phosphorescence host materials, and can be used together with various common phosphorescent materials, such as blue, green, and red phosphorescent materials, like iridium (Ir), platinum (Pt), osmium (Os), copper (Cu), rhodium (Rh), europium (Eu), and ruthenium (Ru) metal complexes. Furthermore, by doped with various common phosphorescent materials, such as blue, green, and red phosphorescent materials, like iridium (Ir), platinum (Pt), osmium (Os), copper (Cu), rhodium (Rh), europium (Eu), and ruthenium (Ru) metal complexes, the wavelength irradiated from the light-emitting layer can be adjusted according to actual needs.

In this embodiment, the bis-triphenylsilyl compound can be applied in an organic electroluminescence and/or phosphorescence device, especially used as a host material, an electron transport material, or a hole transport material. The bis-triphenylsilyl compound can also be applied as an electron transport material or a hole transport material in other organic electronic device. The organic electronic device can be a solar cell, an organic thin film transistor, an organic photoconductor, or other organic semiconducting device well-known to those who are skilled in the art.

In a second embodiment of the invention, an organic light emitting device is disclosed. Generally, the color of light emitted by the organic light emitting device is determined by the fluorescent organic material in the device. Therefore, by doping small amount of guest emitters with high luminance efficiency in host emitters, the recombination efficiency of carriers can be increased. These guest emitters have smaller energy gap, higher luminance efficiency, and shorter recombination lifetime than the host emitters. Therefore, the excitons of the host emitters quickly transfer to the guest emitters through energy transition to carry out recombination effectively. Besides increasing luminance efficiency, the color of the emitted light covers the whole visible light region.

Generally, guest emitters are used together with host emitters by co-evaporation or dispersion, or by spin coating. Guest emitters receive energy from the excited host emitters through energy transfer or carrier trap to produce different colors, such as red, green, and blue, and to increase luminance efficiency. Besides the above mentioned fluorescence guest emitters, new development in phosphorescence material is also researched. As an organic molecule is excited, one quarter of excited electrons form asymmetric spin siglet state and release energy through fluorescence. However, three quarters of excited electrons form symmetric spin triplet state but do not release energy through radiated phosphorescence to thereby lose efficiency. At present, the material capable of releasing the triplet-state energy of the excited electrons through radiated phosphorescence usually is an organic metallic compound having a center transition metal, such as osmium (Os), iridium (Ir), platinum (Pt), europium (Eu), ruthenium (Ru), etc., and the ligand of the organic metallic compound is a nitrogen-containing heterocyclic compound.

According to this embodiment, the organic light emitting device comprises a pair of electrodes and at least one organic layer provided between the electrodes. The at least one organic layer comprises one light-emitting layer and at least one of the organic layers comprises one bis-triphenylsilyl compound, having the following general structure:

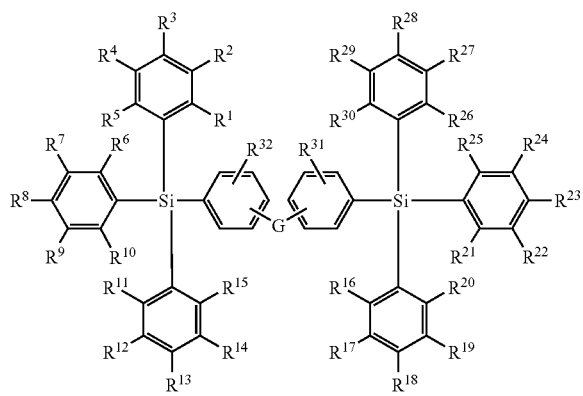

The above G represents any atomic moiety or single bond of aryl group, cyclene group, or heterocyclic ring group. As G represents a single bond, in the above mentioned structure, aryl groups on the two sides of G is bonded with one single bond. The aryl group, cyclene group, or heterocyclic ring group each can further comprise a substituent. The substituent is selected from the group consisting of the following: H atom, halogen atom (such as F, Cl, Br, I); aryl group; halogen substituted aryl group; C1-C20 haloalkyl substituted aryl group; aralkyl group; C1-C20 haloalkyl substituted aralkyl group; aryl substituted C1-C20 alkyl group; C1-C20 alkyl group, C1-C20 cycloalkyl group (such as methyl, ethyl, butyl, cyclohexyl); C1-C20 alkoxy group; amino group; aryl substituted amino group; C1-C20 alkyl substituted amino group; nitrile group; nitro group; carbonyl group; cyano group (—CN); substituted aromatic amino group; aryl phosphoryl (P=O) group, Si-containing aryl group; and heterocyclic ring group.

The above $R^1$~$R^{32}$ can be identical or different and $R^1$~$R^{32}$ are independently selected from the group consisting of the following: H atom, halogen atom (such as F, Cl, Br, I); aryl group; halogen substituted aryl group; C1-C20 haloalkyl substituted aryl group; C1-C20 haloalkyl substituted aralkyl group; aryl substituted C1-C20 alkyl group; C1-C20 alkyl group, C1-C20 cycloalkyl group (such as methyl, ethyl, butyl, cyclohexyl); C1-C20 alkoxy group; amino group; aryl substituted amino group; C1-C20 alkyl substituted amino group; nitrile group; nitro group; carbonyl group; cyano group (—CN); substituted aromatic amino group; aryl phosphoryl (P=O) group; Si-containing aryl group; and heterocyclic ring group.

The aryl group comprises phenyl, naphthyl, diphenyl, anthryl, pyrenyl, phenanthryl, fluorene, or other multi-phenyl group.

The heterocyclic ring group can be pyrane, pyrroline, furan, benzofuran, thiophene, benzothiophene, pyridine, quinoline, isoquinoline, pyrazine, pyrimidine, pyrrole, pyrazole, imidazole, indole, thiazole, isothiazole, oxazole, isoxazole, benzothiazole, benzoxazole, 1,2,4-triazole, 1,2,3-triazole, 1,2,3,4-tetraazole, phenanthroline, or other heterocyclic aryl group.

In a preferred example of this embodiment, the bis-triphenylsilyl compound structure is applied in the light-emitting layer of the organic light emitting device. According to another preferred example of this embodiment, the bis-triphenylsilyl compound structure is applied as a host material in the light-emitting layer of the organic light emitting device. The light-emitting layer can further comprise a guest emitting material and the guest emitting material comprises a transition metal complex. The transition metal of the transition metal complex can be selected from the group consisting of the following: iridium (Ir), platinum (Pt), osmium (Os), copper (Cu), rhodium (Rh), europium (Eu), and ruthenium (Ru). The guest emitting material can be a blue, green, or red phosphorescence material. According to another preferred example of this embodiment, the bis-triphenylsilyl compound structure can be applied in a hole transport layer of the organic light emitting device. According to another preferred example of this embodiment, the bis-triphenylsilyl compound can be applied in an electron transport layer of the organic light emitting device.

General Process for Fabricating an Organic Light Emitting Device

In the device, a glass substrate is used. A positive electrode, a hole-injection layer (can be omitted), a hole-transporting layer, a light-emitting layer, a hole-blocking layer (can be omitted), an electron-transporting layer, an electron-injection layer (LiF) (can be omitted), and a negative electrode are sequentially formed on the substrate. The positive electrode is conductive indium-tin-oxide (ITO) and has a thickness of 100 nm. The light emitting layer is formed by doping phosphorescent material as the guest emitter in the host emitter. Before the evaporation of the organic layers, the ITO glass is cleaned by the purchased cleanser and organic solvent and finally is treated by a UV-ozone cleaner.

FIG. 1 shows a structural schematic diagram illustrating a multi-layer organic light emitting device according to the invention, where the actual thickness of each layer is not related to the drawn dimension in the figure. The layer structure of the organic light emitting device comprises a substrate 100, a positive electrode (+), a hole-injection layer 10, a hole-transporting layer 20, an electron-blocking layer (not shown in the figure), an emitter (light-emitting layer) 30, a hole-blocking layer 40, an electron-transporting layer 50, and a negative electrode (−). The electron-blocking layer, hole-blocking layer 40, and hole-injection layer 10 can be existed or omitted, depending on the requirement of the device. In the above organic light emitting device, the components between the positive and negative electrodes form the electroluminescent medium 400. The emitter (light-emitting layer) 30 is formed by doping phosphorescent material as the dopant in the host compound.

On the other hand, after the OLED device is fabricated, the EL spectra and CIE coordination of the device are measured by Hitachi F-4500 spectra scan spectrometer. In addition, the properties, such as current, voltage, and brightness of the device are measured by Kiethley 2400 programmable voltage-current source. The measurements are carried out at room temperature (about 25° C.) and 1 atm.

EXAMPLE 12

By the general process of fabricating OLED, BSB, pBST, mBSP, mBSP, oBST, mBST-F are used as the host emitting materials and OLEDs are fabricated by doping phosphorescence materials in the host emitting materials. According to this example, the material for the hole-injection layer in the OLED can be CuPc, m-MTDATA, and 2-TNATA shown in the following structure group G1.

Structure group G1

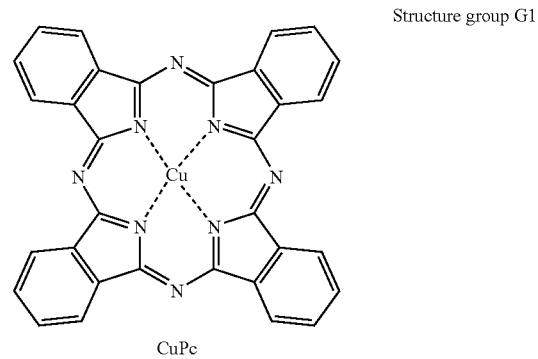

CuPc

-continued
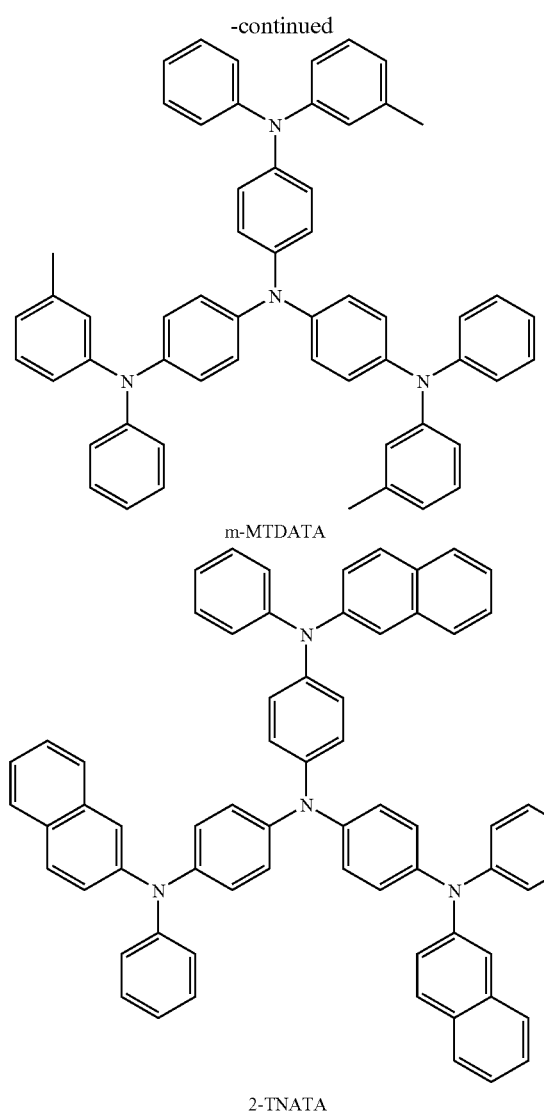
m-MTDATA
2-TNATA
-continued
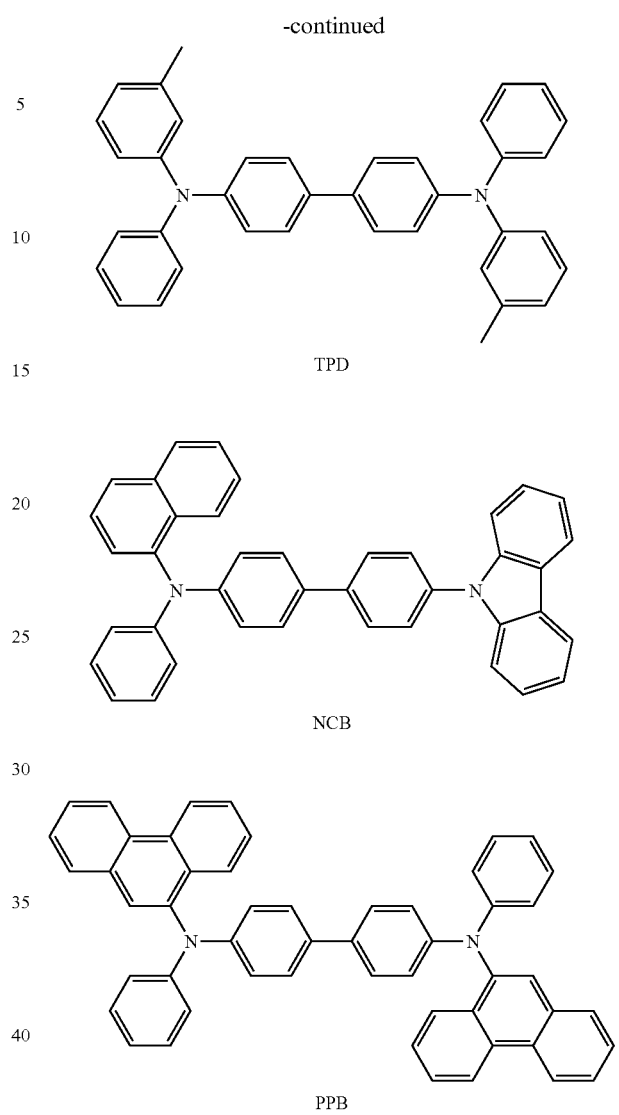
TPD
NCB
PPB
In this example, the material for the hole-transporting layer in the OLED can be NPB, TPD, NCB, PPB, TCTA, MPMP, and HMTPD shown in the following structure group G2 or other aniline compound.
Structure group G2
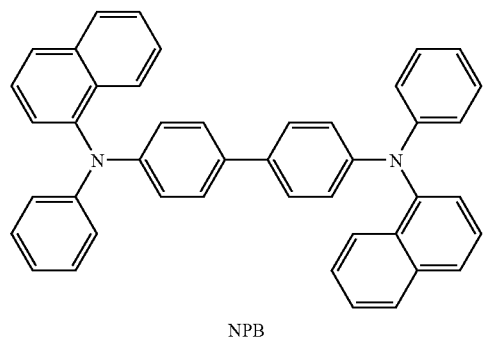
NPB
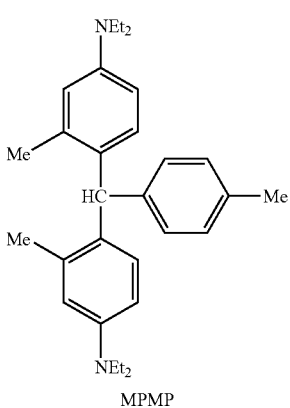
MPMP
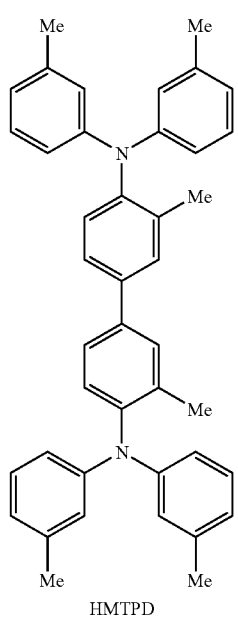
HMTPD

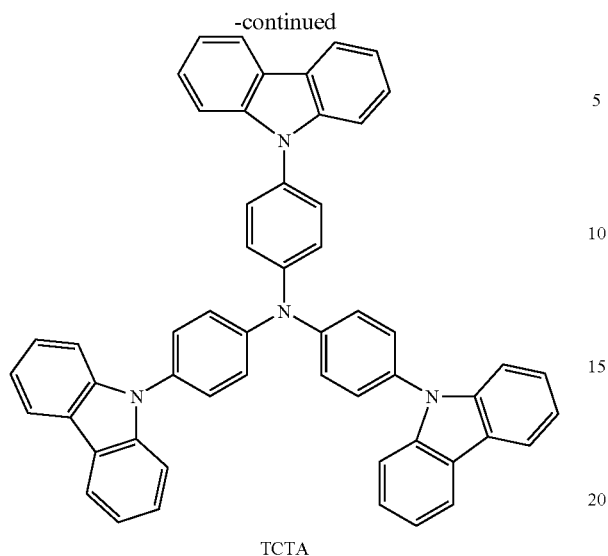

TCTA

In this example, the material for the hole-blocking layer in the OLED can be TPBI shown in the following structure group G3 or BCP, BAlq, PAlq, and SAlq shown in the following structure group G4.

Structure group G3

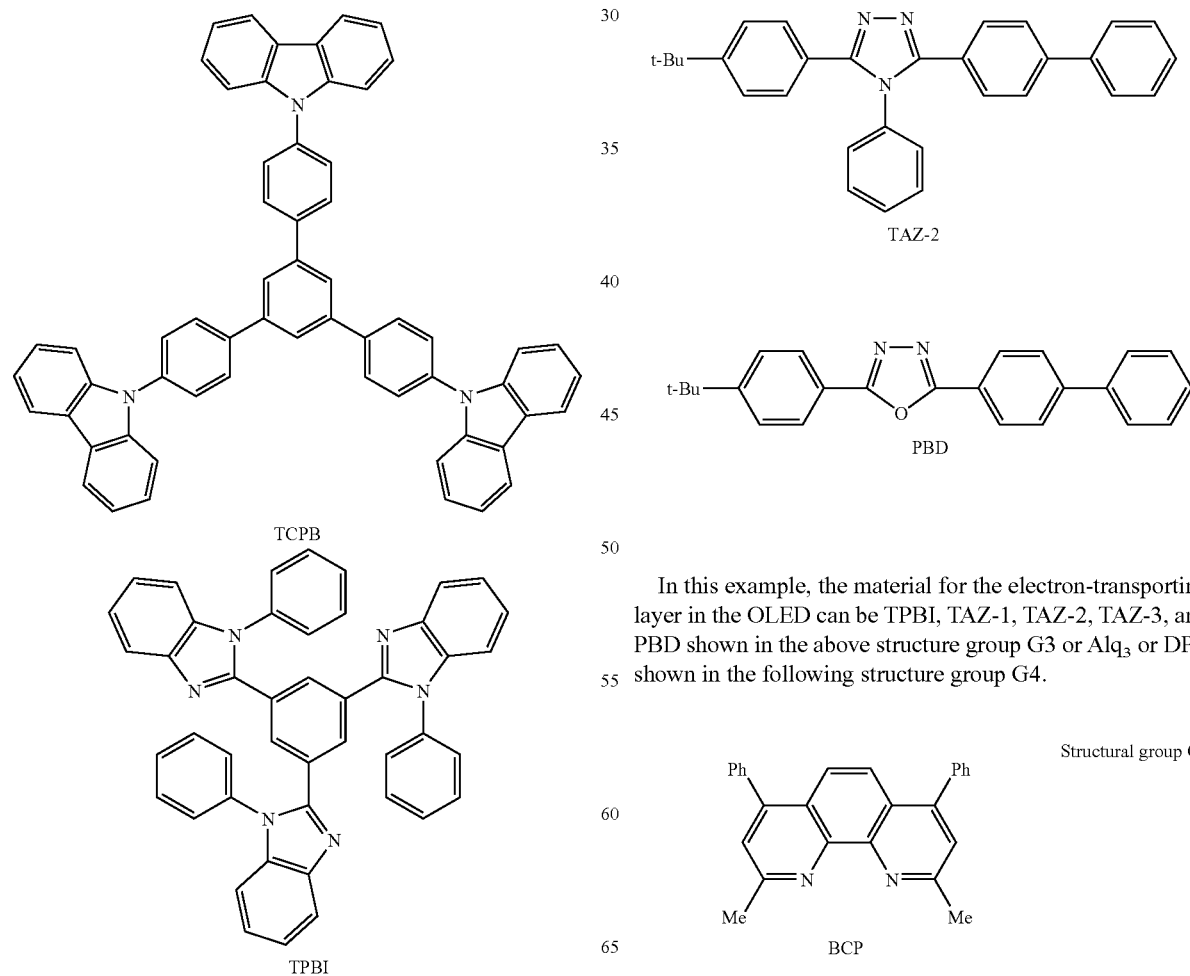

TCPB

TPBI

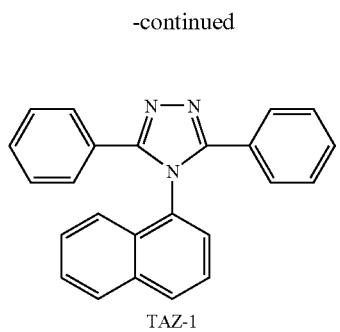

TAZ-1

TAZ-3

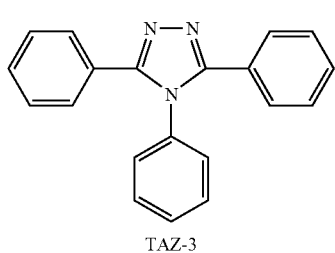

TAZ-2

PBD

In this example, the material for the electron-transporting layer in the OLED can be TPBI, TAZ-1, TAZ-2, TAZ-3, and PBD shown in the above structure group G3 or $Alq_3$ or DPA shown in the following structure group G4.

Structural group G4

BCP

-continued

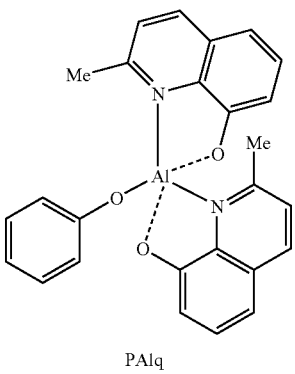
PAlq

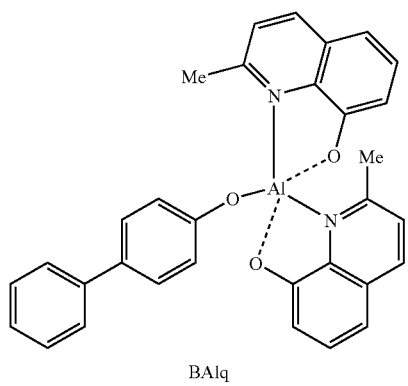
BAlq

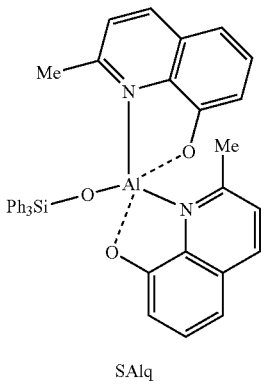
SAlq

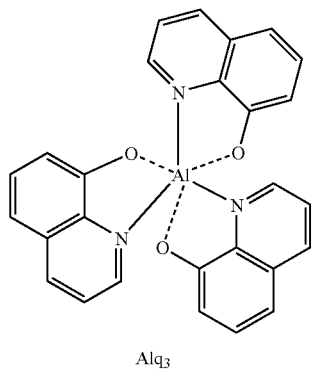
Alq₃

-continued

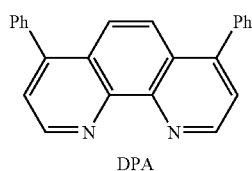
DPA

In the above structure groups G2-G4, Ph represents phenyl, Me represents methyl, Et represents ethyl, and Bu represents butyl.

In this example, the guest emitting material (dopant) used in the OLED can be FIrpic, FIrpytz, FIrN₄, FIr₆, and Ir(pmb)₃ shown in the following structure group G5.

Structure group G5

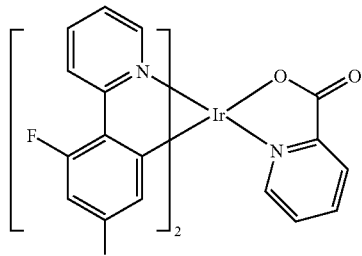
FIrpic

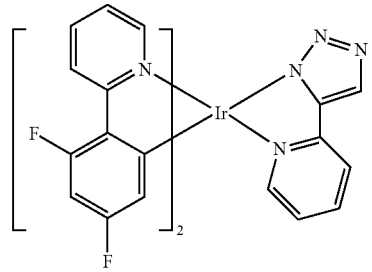
FIrpytz

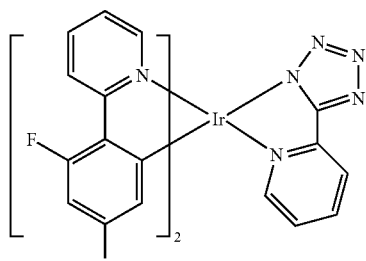
FIrtaz

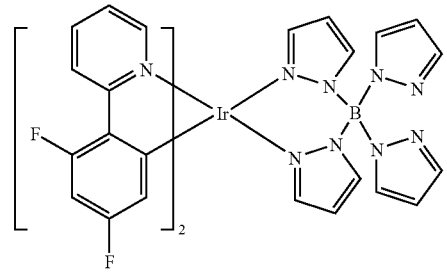
FIr6

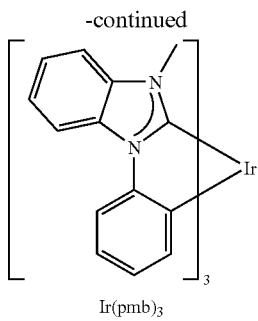

Ir(pmb)₃

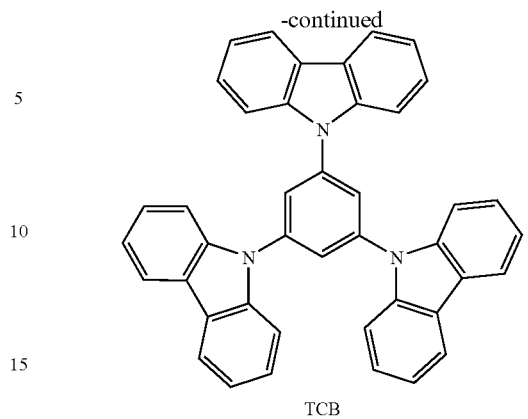

TCB

In this example, the material for the electron-blocking layer in the OLED can be CBP, CCP, mCP, and TCB shown in the following structure group G6.

Structure group G6

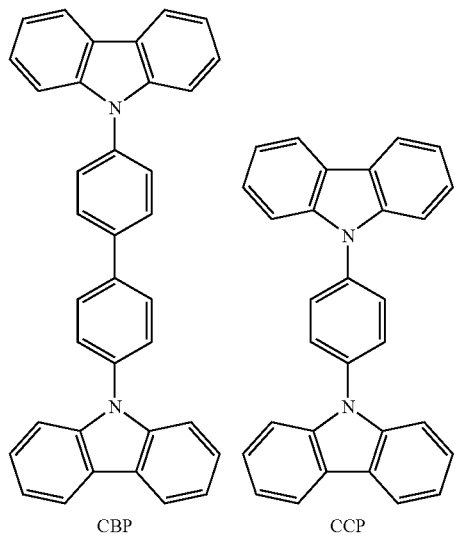

CBP  CCP

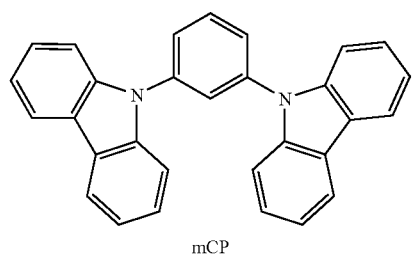

mCP

In the process of fabricating the device, the pressure in the chamber is about smaller than $5\times10^{-6}$ torr during evaporating organic compounds, phosphorescent iridium complexes, and metals. The evaporation rate for the organic films is controlled at about 1.5~2.5 Å/s while the evaporation rate for the phosphorescent iridium complexes is controlled at about 0.05~0.2 Å/s. The evaporation rate for LiF is about 0.5 Å/s. The thickness of the hole-injection layer is about 10~15 nm. The thickness of the hole-transporting layer is about 25~50 nm. The thickness of the hole-blocking layer is about 10~20 nm. The thickness of the electron-transporting layer is about 10~50 nm. The thickness of the electron-injection layer (LiF) is about 0.1 nm. The negative electrode is Mg—Ag alloy or aluminum. The evaporation rate for Mg is about 5 Å/s while that for Ag is 0.5 Å/s (Mg:Ag=10:1). The Mg/Ag co-evaporation with a ratio of 10:1 is carried out to form a film with a thickness of 55 nm. Finally, a silver layer having a thickness of about 100~150 nm as a protection layer is formed. On the other hand, the evaporation rate for aluminum is about 3 Å/s and the thickness is about 100~150 nm.

The structure of each device according to this example is shown in the following.

Device A: TCTA (30)/mCP(20)/FIrpytz:BSB (6%)(30)/BCP (10)/Alq (30)/Mg:Ag
Device B: TCTA (30)/mCP(20)/FIrpytz:pBST (6%)(30)/BCP (10)/Alq (30)/Mg:Ag
Device C: TCTA (30)/mCP(20)/FIrpytz:mBST (6%)(30)/BCP (10)/Alq (30)/Mg:Ag
Device D: TCTA (30)/mCP(20)/FIrpytz:mBSP (6%)(30)/BCP (10)/Alq (30)/Mg:Ag
Device E: TCTA (30)/mCP(20)/FIrpytz:oBST (6%)(30)/BCP (10)/Alq (30)/Mg:Ag
Device F: NPB (30)/mCP(20)/FIrpytz:mBST-F (6%)(30)/ TPBI (30)/LiF(1)/Al The optical properties and efficiency of the devices A~F are measured and shown in Table 1.

TABLE 1

| device | Threshold voltage (V) | Maximum external quantum efficiency (%) (voltage/Volt) | Maximum brightness (cd/m²) (voltage/Volt) | Maximum efficiency (cd/A) (voltage/Volt) | CIE coordinate (8 V) (x, y) | Maximum emitting wavelength (nm) |
|---|---|---|---|---|---|---|
| A | 6.0 | 12.53 (11.5) | 22054 (16.0) | 22.70 (11.5) | 0.13, 0.25 | 462 |
| B | 5.3 | 1.88 (7.5) | 4863 (17.0) | 3.38 (7.5) | 0.15, 0.28 | 472 |

TABLE 1-continued

| device | Threshold voltage (V) | Maximum external quantum efficiency (%) (voltage/Volt) | Maximum brightness (cd/m$^2$) (voltage/Volt) | Maximum efficiency (cd/A) (voltage/Volt) | CIE coordinate (8 V) (x, y) | Maximum emitting wavelength (nm) |
|---|---|---|---|---|---|---|
| C | 5.4 | 8.64 (10.5) | 15133 (15.0) | 14.47 (10.5) | 0.13, 0.24 | 462 |
| D | 6.7 | 9.16 (13.0) | 15256 (18.0) | 18.8 (13.0) | 0.15, 0.30 | 462 |
| E | 4.8 | 10.40 (8.5) | 14203 (14.0) | 17.73 (8.5) | 0.13, 0.23 | 462 |
| F | 6.6 | 10.17 (10.0) | 9014 (15.5) | 15.08 (10.0) | 0.13, 0.21 | 462 |

As shown in the Table 1, the bis-triphenylsilyl compound according to the invention can be used as the phosphorescent host material in the organic light emitting diode and the fabricated device emits blue phosphorescence. Furthermore, the device has high brightness, high current efficiency, and excellent CIE coordinate and thus is valuable for industrial applications.

In this embodiment, the bis-triphenylsilyl compound is applied as a host material in an organic electroluminescence device. On the other hand, the bis-triphenylsilyl compound has the characteristics of electron and hole transport to be applied as an electron transport material or a hole transport material in other electronic devices, besides in an organic electroluminescence device.

According to the invention, as applied in an organic electronic device, the bis-triphenylsilyl compound has the excellent heat stability to make the lifetime of the organic electronic device effectively increased. In addition, the bis-triphenylsilyl compound has high triplet-state energy difference. As applied in an organic light emitting device, the bis-triphenylsilyl compound provides high triplet-state energy difference, which can not be provided by various common blue, green, red phosphorescent host materials, and can be used together with various common phosphorescent materials, such as the iridium (Ir), platinum (Pt), osmium (Os), copper (Cu), rhodium (Rh), europium (Eu), and ruthenium (Ru) metal complexes. Therefore, this invention does have the economic advantages for industrial applications.

Obviously many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

What is claimed is:

1. A bis-triphenylsilyl compound, comprising the following general structure:

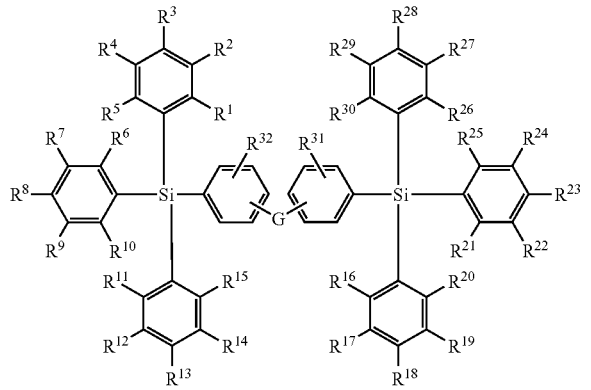

wherein G represents pyridyl based group, wherein said pyridyl based group comprises at least one substituent, wherein $R^1$~$R^{32}$ can be identical or different and $R^1$~$R^{32}$ are independently selected from the group consisting of the following: H atom, halogen atom, halogen substituted aryl group, C1-C20 haloalkyl substituted aryl group, C1-C20 haloalkyl substituted aralkyl group, aryl substituted C1-C20 alkyl group, C1-C20 alkyl group, C1-C20 alkoxy group, amino group, aryl substituted amino group, C1-C20 alkyl substituted amino group, nitrile group, nitro group, carbonyl group, cyano group (—CN), substituted aromatic amino group, aryl phosphoryl (P=O) group, Si-containing aryl group, and heterocyclic ring group.

2. The compound according to claim 1, wherein said pyridyl based group represented by G comprises at least one substituent, wherein said substituent is selected from the group consisting of the following: H atom, halogen atom, aryl group, halogen substituted aryl group, C1-C20 haloalkyl substituted aryl group, C1-C20 haloalkyl substituted aralkyl group, aryl substituted C1-C20 alkyl group, C1-C20 alkyl group, C1-C20 alkoxy group, amino group, aryl substituted amino group, C1-C20 alkyl substituted amino group, nitrile group, nitro group, carbonyl group, cyano group (—CN), substituted aromatic amino group, aryl phosphoryl (P=O) group, Si-containing aryl group, and heterocyclic ring group.

3. The compound according to claim 1, wherein said bis-triphenylsilyl compound comprises a general formula as the following:

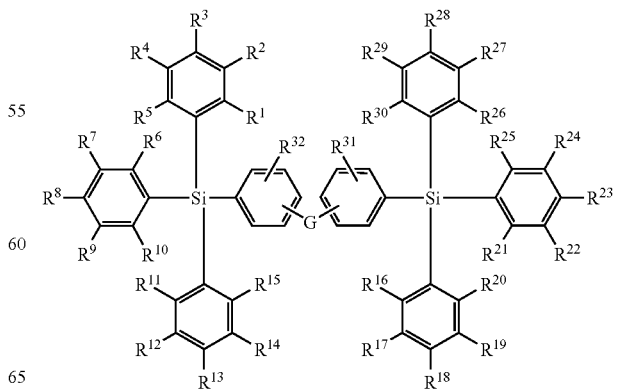

Wherein R³³ is selected from the group consisting of the following: H atom, halogen atom, halogen substituted aryl group, C1-C20 haloalkyl substituted aryl group, C1-C20 haloalkyl substituted aralkyl group, aryl substituted C1-C20 alkyl group, C1-C20 alkyl group, C1-C20 alkoxy group, amino group, aryl substituted amino group, C1-C20 alkyl substituted amino group, nitrile group, nitro group, carbonyl group, cyano group (—CN), substituted aromatic amino group, aryl phosphoryl (P=O) group, Si-containing aryl group, and heterocyclic ring group.

4. The compound according to claim 1, wherein the compound is utilized in an organic electroluminescence and/or phosphorescence device.

5. The compound according to claim 1, wherein the compound is utilized as a host material for an organic electroluminescence and/or phosphorescence device.

6. The compound according to claim 1, wherein the compound is utilized as an electron transport material for an organic electronic device.

7. The compound according to claim 1, wherein the compound is utilized as a hole transport material for an organic electronic device.

8. An organic light emitting device, comprising:
a pair of electrodes; and
at least one organic layer provided between said electrodes; wherein said at least one organic layer comprises one light-emitting layer and at least one of said organic layers comprises one bis-triphenylsilyl compound, having the following general structure:

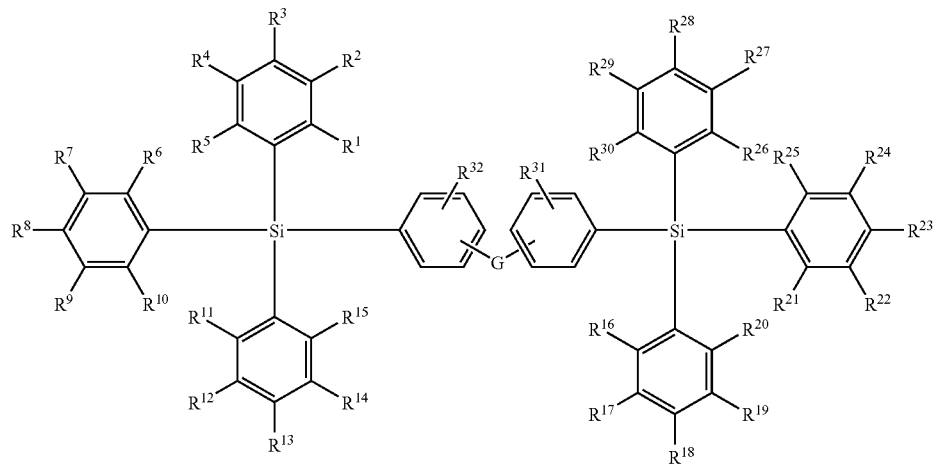

where G represents pyridyl based group, wherein said pyridyl based group comprises at least one substituent, wherein R¹~R³² can be identical or different and R¹~R³² are independently selected from the group consisting of the following: H atom, halogen atom, aryl group, halogen substituted aryl group, C1-C20 haloalkyl substituted aryl group, C1-C20 haloalkyl substituted aralkyl group, aryl substituted C1-C20 alkyl group, C1-C20 alkyl group, C1-C20 cycloalkyl group, C1-C20 alkoxy group, amino group, aryl substituted amino group, C1-C20 alkyl substituted amino group, nitrile group, nitro group, carbonyl group, cyano group (—CN), substituted aromatic amino group, aryl phosphoryl (P=O) group, Si-containing aryl group, and heterocyclic ring group.

9. The device according to claim 8, wherein said pyridyl based group represented by G comprises at least one substituent, wherein said substituent is selected from the group consisting of the following: H atom, halogen atom, aryl group, halogen substituted aryl group, C1-C20 haloalkyl substituted aryl group, C1-C20 haloalkyl substituted aralkyl group, aryl substituted C1-C20 alkyl group, C1-C20 alkyl group, C1-C20 cycloalkyl group, C1-C20 alkoxy group, amino group, aryl substituted amino group, C1-C20 alkyl substituted amino group, nitrile group, nitro group, carbonyl group, cyano group (—CN), substituted aromatic amino group, aryl phosphoryl (P=O) group, Si-containing aryl group, and heterocyclic ring group.

10. The device according to claim 8, wherein said bis-triphenylsilyl compound comprises general formula as the following:

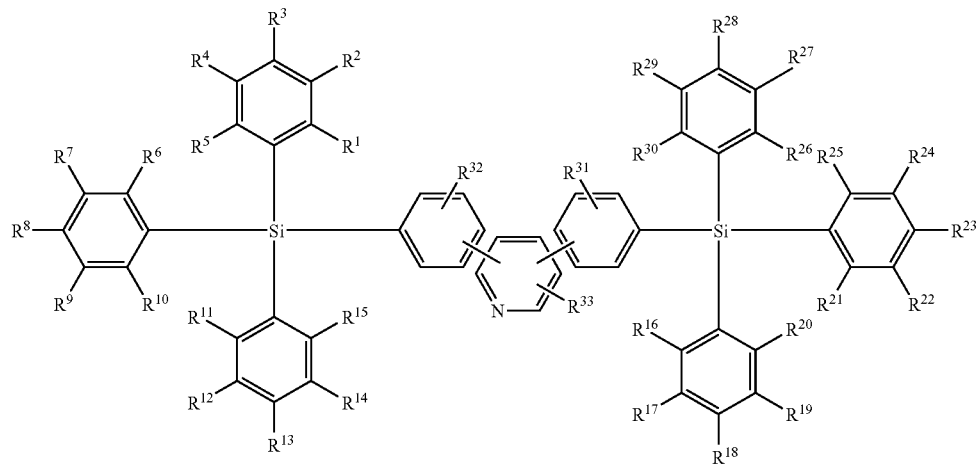

Wherein $R^{33}$ is selected from the group consisting of the following: H atom, halogen atom, halogen substituted aryl group, C1-C20 haloalkyl substituted aryl group, C1-C20 haloalkyl substituted aralkyl group, aryl substituted C1-C20 alkyl group, C1-C20 alkyl group, C1-C20 alkoxy group, amino group, aryl substituted amino group, C1-C20 alkyl substituted amino group, nitrile group, nitro group, carbonyl group, cyano group (—CN), substituted aromatic amino group, aryl phosphoryl (P=O) group, Si-containing aryl group, and heterocyclic ring group.

11. The device according to claim 8, wherein said bis-triphenylsilyl compound is utilized in said light-emitting layer of said organic light emitting device.

12. The device according to claim 8, wherein said bis-triphenylsilyl compound is utilized as a host material in said light-emitting layer of said organic light emitting device.

13. The device according to claim 8, wherein said bis-triphenylsilyl compound is utilized as an electron transport material for said organic light emitting device.

14. The device according to claim 8, wherein said bis-triphenylsilyl compound is utilized as a hole transport material of said organic light emitting device.

15. The device according to claim 8, wherein said light-emitting layer further comprises a guest emitting material and said guest emitting material comprises a transition metal complex.

16. The device according to claim 15, wherein the transition metal of said transition metal complex is selected from the group consisting of the following: iridium (Ir), platinum (Pt), osmium (Os), copper (Cu), rhodium (Rh), europium (Eu), and ruthenium (Ru).

17. The device according to claim 15, wherein said guest emitting material is blue phosphorescent.

18. The device according to claim 15, wherein said guest emitting material is green phosphorescent.

19. The device according to claim 15, wherein said guest emitting material is red phosphorescent.

* * * * *